(12) United States Patent
Yu et al.

(10) Patent No.: US 7,951,374 B2
(45) Date of Patent: May 31, 2011

(54) METHODS FOR INHIBITING STAT3 SIGNALING IN IMMUNE CELLS

(75) Inventors: Hua E. Yu, Glendora, CA (US); Richard Jove, Glendora, CA (US); Marcin Kortylewski, Rancho Cuamonga, CA (US); Drew M. Pardoll, Brookeville, MD (US)

(73) Assignees: University of South Florida, Tampa, FL (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/300,619

(22) Filed: Dec. 14, 2005

(65) Prior Publication Data

US 2006/0127502 A1 Jun. 15, 2006

Related U.S. Application Data

(60) Provisional application No. 60/635,900, filed on Dec. 14, 2004.

(51) Int. Cl.
*A61K 39/00* (2006.01)
(52) U.S. Cl. .................................. 424/178.1; 424/130.1
(58) Field of Classification Search ........................ None
See application file for complete search history.

(56) References Cited

U.S. PATENT DOCUMENTS

| | | | |
|---|---|---|---|
| 5,766,947 A | 6/1998 | Rittershaus et al. | |
| 5,849,790 A | 12/1998 | Palmer et al. | |
| 6,019,966 A | 2/2000 | Coleman et al. | |
| 6,100,090 A | 8/2000 | Monia et al. | |
| 6,265,160 B1 | 7/2001 | Leonard | |
| 2004/0038303 A1 | 2/2004 | Unger | |
| 2004/0138189 A1 | 7/2004 | Sebti et al. | |
| 2004/0175369 A1 | 9/2004 | Yu et al. | |
| 2005/0074502 A1 | 4/2005 | Turkson et al. | |
| 2005/0080131 A1 | 4/2005 | Kay et al. | |
| 2005/0288365 A1 | 12/2005 | Kay et al. | |
| 2006/0210536 A1* | 9/2006 | Horvath et al. | 424/93.2 |
| 2007/0031871 A1 | 2/2007 | Jove | |
| 2007/0213288 A1 | 9/2007 | Haura | |

FOREIGN PATENT DOCUMENTS

| | | |
|---|---|---|
| WO | 02/20032 | 3/2002 |
| WO | 02/078617 | 10/2002 |
| WO | 2004/073650 | 9/2004 |
| WO | 2004/080394 | 9/2004 |
| WO | 2005/023824 | 3/2005 |
| WO | 2006/065894 | 6/2006 |

OTHER PUBLICATIONS

Tannock et al, Experimental Chemotherapy in the Basic Science of Oncology, 1992, eds Tannock and Hill.*
Cheung et al, Immunity, 2003, 19:425-436.*
Mapara et al, J Clin Oncol, Mar. 2004 22:1136-1151.*
Gura, Science, 1997, 278:1041-1042.*

Almand, B. et al., "Clinical significance of defective dendritic cell differentiation in cancer," Clin. Cancer Res. (2000) 6:1755-1766.
Alonzi, T. et al., "Induced somatic inactivation of Stat3 in mice triggers the development of a fulminant form of enterocolitis," Cytokine (2004) 26:45-56.
Bartoli, M. et al., "VEGF differentially activates Stat3 in microvascular endothelial cells," FASEB J. (2003) 17:1562-1564.
Benjamin, L.E. et al., "Selective ablation of immature blood vessels in established human tumors follows vascular endothelial growth factor withdrawal," J. Clin. Invest. (1999) 103:159-165.
Blaskovich, M.A. et al., "Discovery of JSI-124 (Cucurbitacin I), a selective Janus kinase/signal transducer and activator of transcription 3 signaling pathway inhibitor with potent antitumor activity against human and murine cancer cells in mice," Cancer Res. (2003) 63:1270-1279.
Bowman, T. et al., "Stat3-mediated Myc expression is required for Src transformation and PDGF-induced mitogenesis," PNAS (2001) 98:7319-7324.
Bromberg, J. et al., "The role of STATs in transcriptional control and their impact on cellular function," Oncogene (2000) 19:2468-2473.
Brown, R.D. et al., "Dendritic cells from patients with myeloma are numerically normal but functionally defective as they fail to up-regulate CD80 (B7-1) expression after huCD4OLT stimulation because of inhibition by transforming growth factor-β1 and interleukin-10," Blood (2001) 98(10):2992-2998.
Caamano, J. et al., "The NK-κB family member RelB is required for innate and adaptive immunity to toxoplasma gondii," J. Immun. (1999) 163:4453-4461.
Catlett-Falcone, R. et al., "Constitutive activation of Stat3 signaling confers resistance to apoptosis in human U266 myeloma cells," Immunity (1999) 10:105-115.
Cheng, F. et al., "A critical role for Stat3 signaling in immune tolerance," Immunity (2003) 19:425-436.
Costa-Pereira, A.P. et al., "Mutational switch of an IL-6 response to an interferon-γ-like response," PNAS (2002) 99(12):8043-8047.
Dankbar, B. et al., "Vascular endothelial growth factor and interleukin-6 in paracrine tumor-stromal cell interactions in multiple myeloma," Blood (2000) 95:2630-2636.
Darnell, J.E., Jr., "Transcription factors as targets for cancer therapy," Nat. Rev. Cancer (2002) 2:740-749.
Deo, D. et al., "Phosphorylation of Stat-3 in response to basic fibroblast growth factor occurs through a mechanism involving platelet-activating factor, JAK-2, and Src in human umbilical vein endothelial cells. Evidence for a dual kinase mechanism," J. Biol. Chem. (2002) 277:21237-21245.
Dhodapkar, M.V. et al., "Antigen-bearing immature dendritic cells induce peptide-specific CD8+ regulatory T cells in vivo in humans," Blood (2002) 100(1):174-177.
Donnelly, R.P. et al., "The interleukin-10 signal transduction pathway and regulation of gene expression in mononuclear phagocytes," J. Interf. Cytok. Res. (1999) 19:563-573.
Dranoff, G. "Cytokines in cancer pathogenesis and cancer therapy," Nature Reviews (2004) 4:11-22.

(Continued)

*Primary Examiner* — Misook Yu
*Assistant Examiner* — Mark Halvorson
(74) *Attorney, Agent, or Firm* — Michael Best & Friedrich LLP

(57) ABSTRACT

Methods of enhancing antitumor activity of an immune cell comprising contacting the immune cell with a Stat3 inhibitor are described. Also described are methods of killing a tumor cell or inhibiting tumor growth in a subject comprising contacting an immune cell of the subject with a Stat3 inhibitor.

14 Claims, 24 Drawing Sheets
(13 of 24 Drawing Sheet(s) Filed in Color)

OTHER PUBLICATIONS

Dunn, G.P. et al., "Cancer immunoediting: from innunosurveillance to tumor escape," Nature (2002) 3(11):991-998.
Ferlazzo, G. et al., "NK cell compartments and their activation by dendritic cells," J. Immu. (2004) 1333-1339.
Ferrara, N., "VEGF and the quest for tumour angiogenesis factors," Nat. Rev. Cancer (2002) 2:795-803.
Forsythe, J.A. et al., "Activation of vascular endothelial growth factor gene transcription by hypoxia-inducible factor 1," Mol. Cell Biol. (1996) 16:4604-4613.
Furumoto, K. et al., "Spleen-derived dendritic cells engineered to enhance interleukin-12 production elicit therapeutic antitumor immune responses," Int. J. Cancer (2000) 87:665-672.
Geldhof, A.B. et al., "Antagonistic effect of NK cells on alternatively activated monocytes: a contribution of NK cells to CTL generation," Blood (2002) 100(12):4049-4058.
Gerber, H.P. et al., "Vascular endothelial growth factor induces expression of the antiapoptotic proteins Bcl-2 and A1 in vascular endothelial cells," J. Biol. Chem. (1998) 273:13313-13316.
Golumbek, P.T. et al., "Treatment of established renal cancer by tumor cells engineered to secrete interleukin-4," Science (1991) 254:713-716.
Grandis, J.R. et al., "Constitutive activation of stat3 signaling abrogates apoptosis in squamous cell carcinogenesis in vivo," PNAS (2000) 97(8):4227-4232.
Hawiger, D. et al., "Dendritic cells induce peripheral T cell unresponsiveness under steady state conditions in vivo," J. Exp. Med. (2001) 194(6):769-779.
Ho, W.Y. et al., "Adoptive immunotherapy: engineering T cell responses as biologic weapons for tumor mass destruction," Cancer Cell (2003) 3:431-437.
Huss, W.J. et al., "Selectively impairs angiogenesis to induce prostate cancer-specific apoptosis," Mol. Cancer Ther. (2003) 2:611-616.
Inoue, M. et al., "VEGF-A has a critical, nonredundant role in angiogenic switching and pancreatic beta cell carcinogenesis," Cancer Cell (2002) 1:193-202.
Kanakaraj, P. et al., "Defective interleukin (IL)-18-mediated natural killer and T helper cell type 1 responses in IL-1 receptor-associated kinase (IRAK)-deficient mice," J. Exp. Med. (1999) 189(7):1129-1138.
Kiertscher, S.M. et al., "Tumors promote altered maturation and early apoptosis of monocyte-derived dendritic cells," J. Immun. (2000) 164:1269-1276.
Klement, G. et al., "Continuous low-dose therapy with vinblastine and VEGF receptor-2 antibody induces sustained tumor regression without overt toxicity," J. Clin. Invest. (2000) 105:R15-24.
Klement, G. et al., "Differences in therapeutic indexes of combination metronomic chemotherapy and an anti-VEGFR-2 antibody in multidrug-resistant human breast cancer xenografts," Clin. Cancer Res. (2002) 8:221-232.
Kobayashi, M. et al., "Toll-like receptor-dependent production of IL-12p40 causes chronic enterocolitis in myeloid cell-specific Stat3-deficient mice," J. Clin. Invest. (2003) 111(9):1297-1308.
Korpelainen, E.I. et al., "Endothelial receptor tyrosine kinases activate the STAT signaling pathway: mutant Tie-2 causing venous malformations signals a distinct STAT activation response," Oncogene (1999) 18:1-8.
Kuhn, R. et al., "Inducible gene targeting in mice," Science (1995) 269:1427-1429.
Lanzavecchia, A. et al., "Regulation of T cell immunity by dendritic cells," Cell (2001) 106:263-266.
Lanzavecchia, A. et al., "The instructive role of dendritic cells on T cell responses: lineages, plasticity and kinetics," Curr. Op. Immun. (2001) 13:291-298.
Laouar, Y. et al., "STAT3 is required for Flt3L-dependent dendritic cell differentiation," Immunity (2003) 19:903-912.
Lee, C.K. et al., "STAT3 is a negative regulator of granulopoiesis but is not required for G-CSF-dependent differentiation," Immunity (2002) 17:63-72.
Lee, C-K. et al., "Distinct requirements for IFNs and STAT1 in NK cell function," J. Immun. (2000) 165:3571-3577.
Liu, K. et al., "Immune tolerance after delivery of dying cells to dendritic cells in situ," J. Exp. Med. (2002) 196(8):1091-1097.

McBride, W.H. et al., "Genetic modification of a murine fibrosarcoma to produce interleukin 7 stimulates host cell infiltration and tumor immunity," Cancer Res. (1992) 52:3931-3937.
Melani, C. et al., "Myeloid cell expansion elicited by the progression of spontaneous mammary carcinomas in c-erbB-2 transgenic BALB/c mice suppresses immune reactivity," Blood (2003) 102(6):2138-2145.
Menetrier-Caux, C. et al., "Inhibition of the differentiation of dendritic cells from CD34+ progenitors by tumor cells: role of interleukin-6 and macrophage colony-stimulating factor," Blood (1998) 92(12):4778-4791.
Mora, L.B. et al., "Constitutive activation of Stat3 in human prostate tumors and cell lines: direct inhibition of Stat3 signaling induces apoptosis of prostate cancer cells," Cancer Res. (2002) 62:6659-6666.
Nefedova, Y. et al., "Hyperactivation of STAT3 is involved in abnormal differentiation of dendritic cells in cancer," J. Immun. (2004) 172:464-474.
Nguyen, K.B. et al., "Coordinated and distinct roles for IFN-$\alpha\beta$, IL-12, and IL-15 regulation of NK cell responses to viral infection," J. Immun. (2002) 169:4279-4287.
Niu, G. et al., "Roles of activated Src and Stat3 signaling in melanoma tumor cell growth," Oncogene (2002) 21:7001-7010.
Niu, G. et al., "Constitutive stat3 activity up-regulates VEGF expression and tumor angiogenesis," Oncogene (2002) 21:2000-2008.
Niu et al., "Gene therapy with dominant-negative Stat3 suppresses growth of the murine melanoma B16 tumor in vivo," Cancer Res. (1999) 59:5059-5063.
Pardoll, D., "Does the immune system see tumors as foreign or self?" Annu. Rev. Immunol. (2003) 21:807-839.
Porter, A. et al., "Tyrosine kinase receptor-activated signal transduction pathways which lead to oncogenesis," Oncogene (1998) 16:1343-1352.
Rak, J. et al., "Oncogenes as inducers of tumor angiogenesis," Cancer Met. Reviews (1995) 14:263-277.
Rak, J. et al., "What do oncogenic mutations have to do with angiogenesis/vascular dependence of tumors?" Cancer Res. (2002) 62:1931-1934.
Rane, S.G. et al., "JAKs, STATs and Src kinases in hematopoiesis," Oncogene (2002) 21:3334-3358.
Ratta, M. et al., "Dendritic cells are functionally defective in multiple myeloma: the role of interleukin-6," Blood (2002) 100(1):230-237.
Repovic, P. et al., "Oncostatin-M induction of vascular endothelial growth factor expression in astroglioma cells," Oncogene (2003) 22:8117-8124.
Shankaran, V. et al., "IFN$\gamma$ and lymphocytes prevent primary tumour development and shape tumour immunogenicity," Nature (2001) 410:1107-1111.
Shen, Y. et al., "Constitutively activated Stat3 protects fibroblasts from serum withdrawal and UV-induced apoptosis and antagonizes the proapoptotic effects of activated Stat1," PNAS (2001) 98(4):1543-1548.
Smyth, M.J. et al., "Differential tumor surveillance by natural killer (NK) and NKT cells," J. Exp. Med. (2000) 191(4):661-668.
Sotomayor, E.M. et al., "Cross-presentation of tumor antigens by bone marrow-derived antigen-presenting cells is the dominant mechanism in the induction of T-cell tolerance during B-cell lymphoma progression," Blood (2001) 98(4):1070-1077.
Spiotto, M.T. et al., "Increasing tumor antigen expression overcomes 'ignorance' to solid tumors via crosspresentation by bone marrow-derived stromal cells," Immunity (2002) 17:737-747.
Spiotto, M.T. et al., "Bystander elimination of antigen loss variants in established tumors," Nature Med. (2004) 10(3):294-298.
Sun, J. et al., "Cucurbitacin Q: a selective STAT3 activation inhibitor with potent antitumor activity," Oncogene (2005) 1-10.
Takeda, K. et al., "Targeted disruption of the mouse Stat3 gene leads to early embryonic lethality," PNAS (1997) 94:3801-3804.
Takeda, K. et al., "Enhanced Th1 activity and development of chronic enterocolitis in mice devoid of stat3 in macrophages and neutrophils," Immunity (1999) 10:39-49.
Turkson et al., "Phosphotyrosyl peptides block Stat3-mediated DNA-binding activity, gene regulation and cell transformation," J. Biol. Chem. (2001) 276:45443-45455.

Turkson, et al., "A novel platinum compound that inhibits constitutive Stat3 signaling and induces cell cycle arrest and apoptosis of malignant cells," J. Biol. Chem. (2005) 280(38):32979-32988.

Turkson, J. et al., "Inhibition of constitutive Stat3 activation by novel platinum complexes with potent antitumor activity," Mol. Cancer Thera. (2004) 3(12):1533-1542.

Turkson, J. et al., "Novel peptidomimetic inhibitors of signal transducer and activator of transcription 3 dimerization and biological activity," Mol. Cancer Thera. (2004) 3(3):261-269.

Turkson, J. et al., "Stat3 activation by Src induces specific gene regulation and is required for cell transformation," Mol. Cell Biol. (1998) 18:2545-2552.

Vicari, A.P. et al., "Tumour escape from immune surveillance through dendritic cell inactivation," Cancer Biol. (2002) 12:33-42.

Vicari, A.P. et al., "Reversal of tumor-induced dendritic cell paralysis by CpG immunostimulatory oligonucleotide and anti-interleukin 10 receptor antibody," J. Exp. Med. (2002) 196(4):541-549.

Wang et al., "Regulation of the innate and adaptive immune responses by Stat3 signaling in tumor cells," Nature Medicine (2004) 10(1):48-54.

Wang, et al., "Influence of SHIP on the NK repertoire and allogeneic bone marrow transplantation," Science (2002) 295:2094-2097.

Wei, S. et al., "Control of lytic function by mitogen-activated protein kinase/extracellular regulatory kinase 2 (ERK2) in a human natural killer cell line: identification of perforin and granzyme B mobilization by functional ERK2," J. Exp. Med. (1998) 187:1753-1765.

Wei, D. et al., "Stat3 activation regulates the expression of vascular endothelial growth factor and human pancreatic cancer angiogenesis and metastasis," Oncogene (2003) 22:319-329.

Wei, L et al., "Interleukin-6 promotes cervical tumor growth by VEGF-dependent angiogenesis via a STAT3 pathway," Oncogene (2003) 22:1517-1527.

Welte, T. et al., "STAT3 deletion during hematopoiesis causes Crohn's disease-like pathogenesis and lethality: a critical role of STAT3 in innate immunity," PNAS (2003) 100(4):1879-1884.

Wood, J.M. et al., "PTK787/ZK 222584, a novel and potent inhibitor of vascular endothelial growth factor receptor tyrosine kinases, impairs vascular endothelial growth factor-induced responses and tumor growth after oral administration," Cancer Res. (2000) 60:2178-2189.

Yahata, Y. et al., "Nuclear translocation of phosphorylated Stat3 is essential for vascular endothelial growth factor-induced human dermal microvascular endothelial cell migration and tube formation," J. Biol. Chem. (2003) 278:40026-40031.

Yu, C-L. et al., "Enhanced DNA-binding activity of a Stat3-related protein in cells transformed by the Src oncoprotein," Science (1995) 269:81-83.

Yu, H. et al., "The STATs of cancer—new molecular targets come of age," Nat. Rev. Cancer (2004) 4:97-105.

Yu, Z. et al., "Signal transducers and activators of transcription 3 (STAT3) inhibits transcription of the inducible nitric oxide synthase gene by interacting with nuclear factor κB," Biochem. J. (2002) 367:97-105.

Yuan, F. et al., "Time-dependent vascular regression and permeability changes in established human tumor xenografts induced by anti-vascular endothelial growth factor/vascular permeability factor antibody," PNAS (1996) 93:14765-14770.

Calvin, D.P. et al., "Inhibition of Stat3 activity with Stat3 antisense oligonucleotide (Stat3-ASO) enhances radiation-induced apoptosis in DU145 prostate cancer cells," Int. J. Radiat. Oncol. Biol. Phys. (2003) 57:S297 Proceedings of the 45th Annual ASTRO Meeting.

Turkson, J. et al., "STAT proteins: novel molecular targets for cancer drug discovery," Oncogene (2000) 19:6613-6626.

Alas, S. et al., "Inhibition of constitutive Stat 3 activity sensitizes resistant non-Hodgkin's lymphoma and multiple myeloma to chemotherapeutic drug-mediated apoptosis," Clin. Cancer Res. (2003) 9:316-326.

Bowman, T. et al., "STATs in oncogenesis," Oncogene (2000) 19:2474-2488.

Buettner, R. et al., "Activated STAT signaling in human tumors provides novel molecular targets for therapeutic intervention," Clin. Cancer Res. (2002) 8:945-954.

Sun et al., "Cucurbitacin Q: a selective STAT3 activation inhibitor with potent antitumor activity," Oncogene (2005) 24:3236-3245.

U.S. Appl. No. 10/894,200, filed Jul. 19, 2004, Haura.

U.S. Appl. No. 11/581,293, filed Oct. 16, 2006, Torres-Roca.

Akira, S. (2000) "Roles of STAT3 defined by tissue-specific gene targeting." Oncogene, 19: 2607-2611.

Alas S, Bonavida B. (2001) "Rituximab inactivates signal tranducer and activation of transcription 3 (STAT3) activity in B-non-Hodgkin's lymphoma through inhibition of the interleukin 10 autocrine/paracrine loop and results in down-regulation of Bcl-2 and sensitization to cytotoxic drugs." Cancer Res 61:5137-44.

Alvarez JV and Frank DA. (2004). "Genome-Wide Analysis of STAT Target Genes" Cancer Biol Ther, 3, 1045-50.

Bromberg J.(2000) "Signal transducers and activators of transcription as regulators of growth, apoptosis and breast development." Breast Cancer Res 2:86-90.

Bromberg JF et al., (1999) "Stat3 as an oncogene." Cell 98:295-303.

Bromberg, J.F. et al., "Stat3 activation is required for cellular transformation by v-src," Mol. Cell Biol. (1998) 18:2553-2558.

Catlett-Falcone R, Dalton WS, Jove R: (1999) "STAT proteins as novel targets for cancer therapy." Curr Opin Oncol 11:490-496.

Darnell JE, Jr. (1997) "STATs and gene regulation" Science 1997;277:1630-5.

Darnell JE, Jr., Kerr IM, Stark GR: (1994) "Jak-STAT pathways and transcriptional activation in response to IFNs and other extracellular signaling proteins." Science 264:1415-21.

Epling-Burnette PK, et al.(2001) "Inhibition of STAT3 signaling leads to apoptosis of leukemic large granular lymphocytes and decreased Mcl-1 expression." J Clin Invest 107:351-62.

Ezzat AA, Rahal M, Ajarim D, et al: (2003) "Dose dense neoadjuvant sequential chemotherapy in the management of locally advanced breast cancer: A phase II study [Abstract 202]." Proc Am Soc Clin Oncol 22:51, 2003.

Fukada, T. et al., "Two signals are necessary for cell proliferation induced by a cytokine receptor gp130: involvement of STAT3 in anti-apoptosis," Immunity (1996) 5:449-460.

Garcia, R. et al., "Activation of STAT transcription factors in oncogeqic tyrosine kinase signaling," J. Biomed. Sci. (1998) 5:79-85.

Grandis Jr, et al. (1998) "Requirement of Stat3 but not Stat1 activation for epidermal growth factor receptor-mediated cell growth in vitro." J Clin Invest 102:1385-92.

Grandis, R.J. et al., "Epidermal growth factor receptor-mediated stat3 signaling blocks apoptosis in head and neck cancer," Laryngoscope (2000b) 110:868-874.

Hanahan D and Weinberg RA. (2000). "The Hallmarks of Cancer" Cell, 100, 57-70.

Hao D and Rowinsky EK. (2002). "Inhibiting Signal Transduction: Recent Advances in the Development of Receptor Tyrosine Kinase and Ras Inhibitors" Cancer Invest, 20, 387-404.

Hirano, T., Ishihara, K, and Hibi, M. (2000) "Roles of STAT3 in mediating the cell growth. differentiation and survival signals relayed through the IL-6 family of cytokine receptors." Oncogene, 19: 2548-2556.

Jing, N. et al., "G-quartet oligonucleotides: a new class of signal transducer and activator of transcription 3 inhibitors that suppresses growth of prostate and breast tumors through induction of apoptosis," Cancer Res. (2004) 64:6603-6609.

Karras JG, et al.(2000) "STAT3 regulates the growth and immunoglobulin production of BCL (1) B cell lymphoma through control of cell cycle progression." Cell Immunol 202:124-35.

Kotenko, S.V. et al., "Jak-Stat signal transduction pathway through the eyes of cytokine class II receptor complexes," Oncogene (2000) 19:2557-2565.

Kris MG, Natale RB, Herbst RS, et al. (2003) "Efficacy of gefitinib, an inhibitor of the epidermal growth factor receptor tyrosine kinase, in symptomatic patients with non-small cell lung cancer: a randomized trial." Jama 290:2149-58.

Levy, D.E. et al., "Stats: transcriptional control and biological impact," Nature Rev. (2002) 3:651-662.

Lin TS, Mahajan S, Frank DA. (2000) "STAT signaling in the pathogenesis and treatment of leukemias." Oncogene 19:2496-2504.

Redell MS and Tweardy DJ. (2005)."Targeting Transcription Factors for Cancer Therapy" Curr Pharm Des, 11, 2873-87.

Schindler, C. et al., "Transcriptional responses to polypeptide ligands: the JAK-STAT pathway," Annu. Rev. Biochem. (1995) 64:621-651.

Smith, P. D. and Crompton, M. R. (1998) "Expression of v-src in mammary epithelial cells induces transcription via STAT3." *Biochem J*, 331: 381-385.

Song JI, Grandis Jr. (2000) "STAT signaling in head and neck cancer." *Oncogene* 19:2489-95.

Strobl JS, Wonderlin WF and Flynn DC. (1995). "Mitogenic Signal Transduction in Human Breast Cancer Cells" *Gen Pharmacol*, 26, 1643-9.

Turkson J. (2004) "STAT proteins as novel targets for cancer drug discovery." *Expert Opin Ther Targets* 8:409-22.

Zhang Y, et al. (2000) "Activation of Stat3 in v-Src-transformed fibroblasts requires cooperation of Jak1 kinase activity." *J Biol Chem* 275:24935-44.

Zhong, Z., Wen, Z., and Darnell, J. E., Jr.(1994) "Stat3: a STAT family member activated by tyrosine phosphorylation in response to epidermal growth factor and interleukin-6." *Science*, 264: 95-98.

Burke, W.M. et al., "Inhibition of constitutively active Stat3 suppresses growth of human ovarian and breast cancer cells," Oncogene (2001) 20:7925-7934.

Cheng, J.Q. et al., "Amplification of AKT2 in human pancreatic cancer cells and inhibition of AKT2 expression and tumorigenicity by antisense RNA," Proc. Natl. Acad. Sci. USA (1996) 93:3636-3641.

Dhir, R. et al., "Stat3 activation in prostatic carcinomas," The Prostate (2002) 51:241-246.

Kong, B. et al., "IL-6 antisense-mediated growth inhibition of a choriocarcinoma cell line: an intracellular autocrine growth mechanism," Gynecologic Oncology (1996) 63:78-84.

Lin, J. et al., "The phosphatidylinositol 3'-kinase pathway is a dominant growth factor-activated cell survival pathway in LNCaP human prostate carcinoma cells," Cancer Res. (1999) 59:2891-2897.

Meydan, N. et al., "Inhibition of acute lymphoblastic leukaemia by a Jak-2 inhibitor," Nature (1996) 379:645-648.

Murillo, H. et al., "Role of PI3K signaling in survival and progression of LNCaP prostate cancer cells to the androgen refractory state," Endocrinology (2001) 142(11):4795-4805.

Scherer, L.J. et al., "Approaches for the sequence-specific knockdown of mRNA," Nature Biotech. (2003) 21(12):1457-1465.

Thabard, W. et al., "IL-6 upregulates its own receptor on some human myeloma cell lines," Cytokine (2001) 14(6):352-356.

Valdembri, D. et al., "In vivo activation of JAK2/STAT-3 pathway during angiogenesis induced by GM-CSF," FASEB J. (2002) 16(2):225-227.

Wei, L-H. et al., "The anti-apoptotic role of interleukin-6 in human cervical cancer is mediated by up-regulation of Mcl-1 through a PI 3-K/Akt pathway," Oncogene (2001) 20:5799-5809.

Yang, L. et al., "Akt/protein kinase B signaling inhibitor-2, a selective small molecule inhibitor of Akt signaling with antitumor activity in cancer cells overexpressing Akt," Cancer Res. (2004) 64:4394-4399.

Yang, L. et al., "Interleukin-6 differentially regulates androgen receptor transactivation via PI3K-Akt, STAT3, and MAPK, three distinct signal pathways in prostate cancer cells," Biochem. Biophys. Res. Comm. (2003) 305:462-469.

International Search Report and Written Opinion of International Searching Authority for International Application No. PCT/US2005/45225 dated Oct. 18, 2006.

United States Office Action for U.S. Appl. No. 11/102,911 dated Mar. 21, 2008.

International Search Report and Written Opinion of International Searching Authority for International Application No. PCT/US2005/12081 dated Nov. 18, 2005.

Office Action from European Patent Office for European Patent Application No. 05778394.6 dated Jul. 12, 2007.

Office Action from European Patent Office for European Patent Application No. 05778394.6 dated Aug. 14, 2008.

International Search Report and Written Opinion of International Searching Authority for International Application No. PCT/US2006/28108 dated Sep. 12, 2007.

International Search Report and Written Opinion of International Searching Authority for International Application No. PCT/US2006/40457 dated Jul. 16, 2007.

United States Office Action for U.S. Appl. No. 11/490,316 dated Dec. 30, 2008 (9 pages).

European Office Action for Application No. 05778394.6 dated Dec. 18, 2007 (3 pages).

United States Office Action for U.S. Appl. No. 11/102,911 dated Nov. 26, 2008 (14 pages).

United States Patent Office Action for U.S. Appl. No. 11/102,911 dated Jul. 22, 2009 (15 pages).

United States Patent Office Action for U.S. Appl. No. 11/102,911 dated Mar. 16, 2010 (12 pages).

United States Office Action for U.S. Appl. No. 11/490,316 dated Oct. 5, 2009 (11 pages).

\* cited by examiner

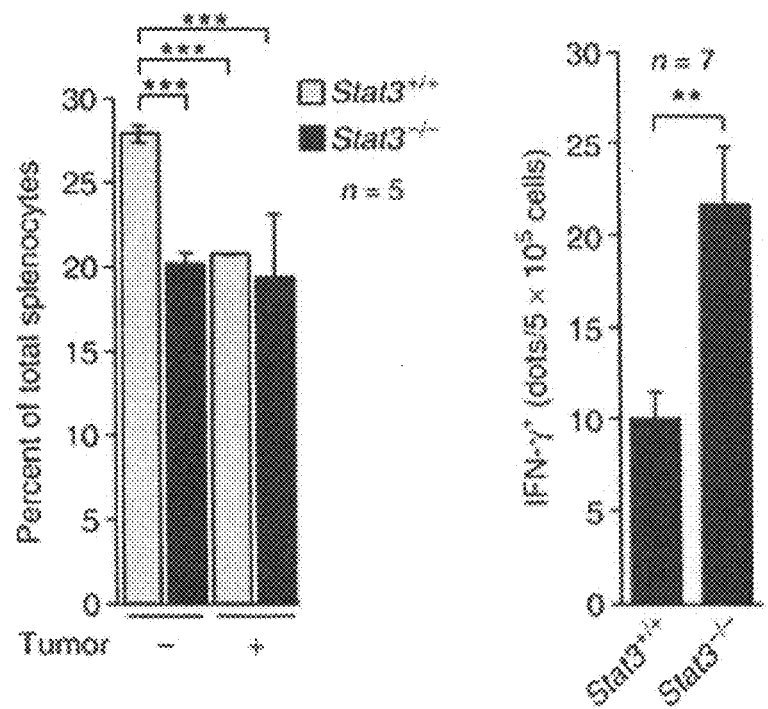
FIG. 18  FIG. 19
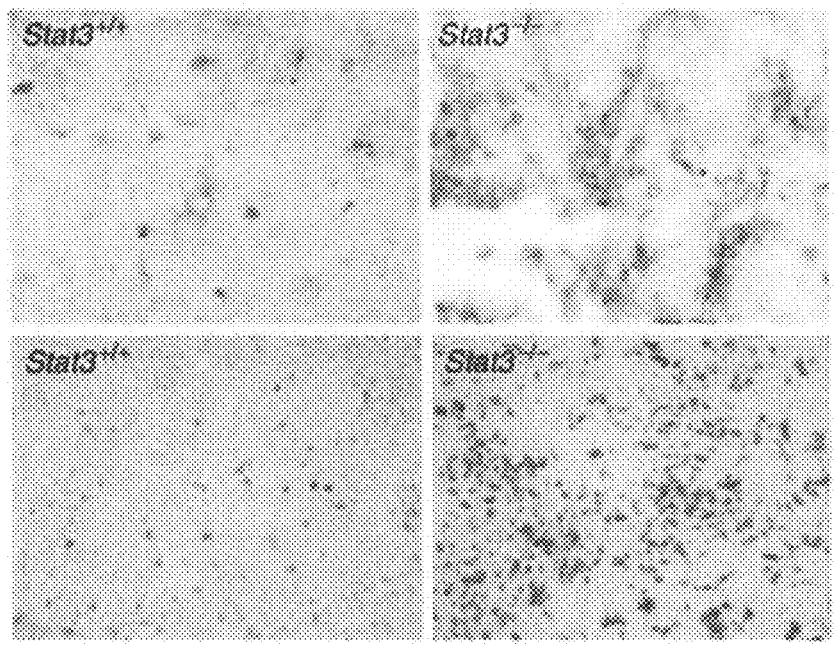
FIG. 20

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1

-continued actcaaactg ccctcctgct                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
tctgaagaaa ctgcttgatt                              20

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 3
gccacaatcc gggcaatct                               19

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
tggctgcagt ctgtagaagg                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
tttctgttct agatcctgca                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
tagttgaaat caaagtcatc                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ttccattcag atcttgcatg                              20

<210> SEQ ID NO 8
<211> LENGTH: 20
<212> TYPE: DNA
<213> ORGANISM: Artificial Sequence
<220> FEATURE:

-continued

```
<223> OTHER INFORMATION: Synthetic Oligonucleotide

<400> SEQUENCE: 8
tctgttccag ctgctgcatc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tcactcacga tgcttctccg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
gagttttctg cacgtactcc                                               20
```

METHODS FOR INHIBITING STAT3 SIGNALING IN IMMUNE CELLS

CROSS-REFERENCE TO RELATED APPLICATIONS

This application claims benefit of priority under 35 USC §119 to U.S. Provisional Application Ser. No. 60/635,900, filed Dec. 14, 2004, which is incorporated herein by reference in its entirety.

STATEMENT REGARDING FEDERALLY SPONSORED RESEARCH OR DEVELOPMENT

This invention was made with United States government support awarded by the National Institutes of Health and National Cancer Institute (Grant No. R01 CA89693). The United States government has certain rights in this invention.

REFERENCE TO A SEQUENCE LISTING

This application contains a Sequence Listing. The Sequence Listing, submitted on one (1) diskette, is incorporated herein by reference in its entirety.

INTRODUCTION

Signal transduction is classically thought to employ a series of second messengers or intermediaries that act sequentially to relay extracellular stimuli to the nucleus. However, studies of interferon (IFN)-dependent gene expression have led to the discovery of pathways that signal directly from the cell surface to the nucleus. Essential mediators of signaling in these direct pathways are referred to as signal transducers and activators of transcription, or "STATs." Members of the STAT family of transcription factors become activated by tyrosine kinases in the cytoplasm, dimerize, and then migrate to the nucleus where they directly regulate gene expression. Thus, STATs perform a dual function with respect to signal transduction and gene regulation, thereby obviating the need for additional intermediaries.

Seven mammalian STAT family members (Stat1 through Stat6, with Stat5a and Stat5b representing distinct genes) have been molecularly cloned and share common structural elements. Structural motifs common to most STAT family members and their associated functions have been elucidated based on biochemical and molecular studies. Each STAT molecule contains an Src-homology 2 (SH2) domain, a common protein-protein interaction domain among signaling proteins. Monomeric, inactive STAT proteins associate with each other to form active dimers through a key phosphotyrosine (pY) residue, which binds to the SH2 domain of another STAT monomer. Furthermore, such reciprocal SH2-pY interactions are required for STAT functions, including nuclear transport and DNA binding. Thus, the activating event in STAT signaling is tyrosine phosphorylation. The DNA-binding domain resides in the N-terminal portion of the STAT molecule. Located within the C-terminal portion is the transactivation domain, which contains a serine residue, the phosphorylation of which is required for maximal transcriptional activity.

Deregulated activation of STATs is thought to contribute to neoplastic transformation. In contrast to normal signaling, aberrant receptor activation or protein tyrosine kinase (PTK) activity induces constitutive STAT signaling in oncogenesis. For example, abnormal activation of Stat3, a member of the STAT family, has been linked to a number of cancers. In particular, Stat3 is abnormally activated with high frequency in the carcinomas of the breast, head and neck squamous cell carcinoma, ovarian carcinoma, and skin melanomas. Abnormal Stat3 activation also correlates with the progression of diverse hematopoietic malignancies, such as various leukemias and lymphomas, and Stat3 is frequently activated in both multiple myeloma cell lines and tumor cell lines derived from patient bone marrows.

The inventors and others have investigated the effects of targeting Stat3 signaling in cancer cells and have demonstrated that inhibition of Stat3 suppresses tumor growth and induces tumor regression (see e.g., U.S. Application Publication No. 20050074502 and Niu et al., "Gene Therapy with Dominant-negative Stat3 Suppresses Growth of the Murine Melanoma B16 Tumor in Vivo," Cancer Res. 59, 5059-63 (1999)). Moreover, it has been shown that constitutive activation of Stat3 in tumors negatively regulates induction of adaptive immunity by blocking tumor expression of proinflammatory mediators (Wang et al. "Regulation of the innate and adaptive immune responses by Stat3 signaling in tumor cells," Nature Medicine 10:1, 48-54 (2004)). Indirectly decreasing Stat3 expression or function in antigen presenting cells (APCs) by co-culture with tumor cells having decreased Stat3 function has also been shown to have anti-tumor effects in mice (U.S. Application Publication 20040175369). However, direct inhibition of Stat3 signaling in immune cells has not previously been evaluated.

BRIEF SUMMARY

In one aspect, the invention concerns methods for enhancing the antitumor activity of an immune cell by contacting the immune cell with a Stat3 inhibitor.

In another aspect, the invention provides methods for killing a tumor cell or inhibiting tumor growth in a subject by contacting an immune cell of the subject with a Stat3 inhibitor.

BRIEF DESCRIPTION OF THE FIGURES

The patent or application file contains at least one drawing executed in color. Copies of this patent or patent application publication with color drawings will be provided by the Patent Office upon request and payment of the required fee.

FIG. 18 is a graphical representation showing percentages of T cells (CD3$^+$) in spleens of tumor-free and B16 tumor-bearing mice with and without Stat3 in their hematopoietic system as determined by flow cytometry analysis. Shown are the means±s.d.; n=5, P<0.001.

FIG. 19 is a graphical representation showing results of an ELISPOT assay for IFN-γ expressed by T cells from B16 tumor-bearing mice. Data shown are mean numbers of p15E-specific IFN-γ-producing spots from seven to nine separate mice per group analyzed individually. **P=0.0092.

FIG. 20 shows results of immunohistochemical analysis of B16 (top) and MB49 (bottom) tumor tissue sections prepared from Stat3$^{+/+}$ and Stat3$^{-/-}$ mice. Red indicates CD8 staining; blue indicates CD4 staining.

DETAILED DESCRIPTION

Figure 1:
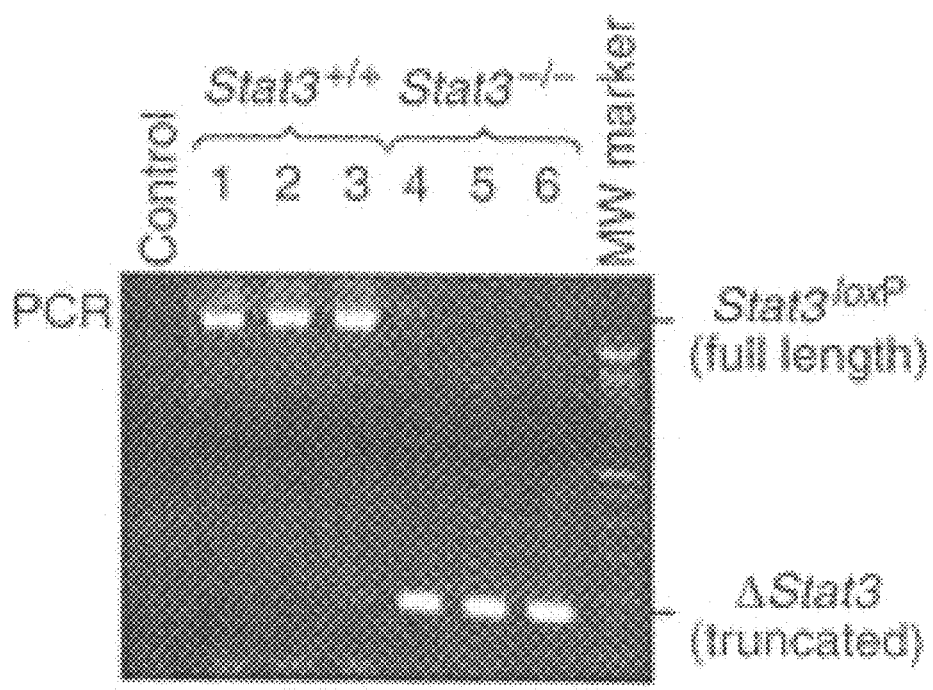
FIG. 1 shows results of PCR analysis of genomic DNA from bone marrow after poly(I:C) treatment with primer sets that distinguish full-length $Stat3^{loxP}$ and Stat3-deleted alleles.

The inventors have discovered that blocking Stat3 in hematopoietic cells induces a complex antitumor response that includes both innate and adaptive elements. Moreover, dendritic cells lacking Stat3 signaling in tumor-bearing hosts have heightened immune function in comparison to tumor-infiltrating dendritic cells having constitutively activated Stat3. B16 antigen-specific T cells from Stat3$^{-/-}$ mice bearing B16 tumors become activated without vaccination. Mice with a Stat3$^{-/-}$ hematopoietic compartment display enhanced T-cell infiltration in tumors. Stat3 blockade-induced antitumor effects are T-cell dependent. Lack of Stat3 signaling in neutrophils and NK cells, at least when exposed to the tumor microenvironment, leads to significantly enhanced antitumor cytolytic activities. Thus, inhibiting Stat3 activity in multiple hematopoietically-derived cell types restores tumor immune surveillance, and targeting Stat3 in these cells within the tumor microenvironment evokes therapeutic antitumor immunity. Importantly, the above effects were observed independent of the sensitivity of the tumor to the Stat3 inhibitor. In other words, antitumor effects were observed even in tumors insensitive to Stat3 blockade-mediated apoptosis.

In accordance with the above discoveries, one embodiment of the invention provides a method of enhancing antitumor activity of an immune cell comprising contacting the immune cell with a Stat3 inhibitor. As used herein, an immune cell is an effector, helper or regulator of adaptive and/or innate immunity, or is a hematopoietic progenitor or stem cell which differentiates into a mature immune cell. Suitable immune cells which may be targeted for inhibition of Stat3 include, but are not limited to, dendritic cells, natural killer cells, T cells and neutrophils, as well as progenitor or stem cells. Most suitably, the immune cell is a tumor infiltrating immune cell.

"Contacting an immune cell" refers to the direct targeting of an immune cell with a Stat3 inhibitor, either by targeted delivery for in vivo administration, or by incubation with a Stat3 inhibitor ex vivo or in vitro. The term "contacting an immune cell," as used herein, expressly does not include indirect methods of inhibiting Stat3 in immune cells, such as by co-culturing immune cells with tumor cells having reduced Stat3 signaling or contacting immune cells with supernatant from cultured tumor cells having reduced Stat3 signaling.

As used herein, a "tumor" refers to any manifestation of a hyperproliferative disorder, including, e.g., a solid tumor mass, a system of tumor nodules and/or cancer of the hematopoietic system. Examples of tumors suitably treated in accordance with the presently described methods include, but are not limited to, carcinomas of the breast, head and neck squamous cell carcinomas, prostate carcinomas, ovarian carcinomas, skin melanomas, leukemias and lymphomas. As will be understood, any neoplastic disease characterized by abnormal Stat3 activation is suitably ameliorated as described herein. "Enhancing antitumor immunity" refers to improving cytolytic, presentation or helper (i.e., cytokine secretion) functions of immune cells, resulting in, e.g., tumor cell killing, induction of tumor cell apoptosis, reduction in tumor volume, reduction of tumor burden, eradication of established tumors, inhibition of tumor cell proliferation, reduction of metastasis and/or enhanced survival of tumor-bearing subjects. Methods of assaying for these effects are commonly employed in the art. Antitumor activity is "enhanced" if any of the above listed effects are increased in the presence of immune cells that have been contacted with a Stat3 inhibitor compared to control immune cells that have not been contacted with a Stat3 inhibitor.

As used herein, "inhibition" or "inhibiting" Stat3 in immune cells encompasses both pharmacological blocking of Stat3 and genetic deletion of or interference with Stat3 coding sequences in immune cells. A "Stat3 inhibitor," as used herein, is any agent capable of disrupting Stat3 signaling in an immune cell. As will be appreciated, suitable Stat3 inhibitors include not only agents that directly interfere with binding of Stat3 to its consensus sequence, but also may suitably include agents that interfere with tyrosine phosphorylation required for Stat3 dimerization by, e.g., inhibiting tyrosine kinases and/or SH2-pY interactions. Further suitable agents may interfere with nuclear transport of Stat3 dimers. In addition, structural features of Stat3, such as the DNA binding and transactivation domains, may suitably serve as targets for functional disruption of Stat3. The most suitable agents for inhibiting Stat3 will be those that are potent and selective disruptors of Stat3 signaling activity. Suitable compounds for inhibiting Stat3 in immune cells include platinum (IV) compounds and their pharmaceutically acceptable salts. The term "pharmaceutically-acceptable salts" means salts of the platinum complexes of the invention which are prepared with acids or bases, depending on the particular substituents of the compounds. Examples of a pharmaceutically acceptable base addition salts include sodium, potassium, calcium, ammonium, or magnesium salt. Examples of pharmaceutically acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Platinum (IV) compounds and their pharmaceutically acceptable salts can be prepared using conventional techniques known in the art.

Examples of suitable platinum (IV) compounds include CPA-1, CPA-3 CPA-7, and platinum (IV) tetrachloride. One particularly suitable inhibitor is CPA-7, the structure of which is shown below.

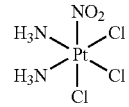

A further platinum (IV) compound suitable for use in methods of inhibiting Stat3 in immune cells is IS3 295 (obtainable from the NCl diversity set, NSC 295558), the structure of which is shown below.

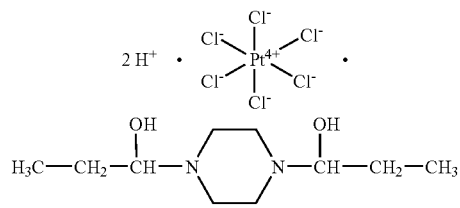

Additional suitable small molecule Stat3 inhibitors include the compounds disclosed in U.S. Application Publication No. 20050080131, which is incorporated herein by reference.

In addition, there are numerous approaches to identifying additional compounds that will disrupt Stat3 signaling in immune cells. Many of these strategies are based on high-throughput screening to identify compounds that are selective for inhibiting specific Stat3 functions in vitro or in vivo. For in vitro screens, the ability of compounds to disrupt Stat3 dimerization or DNA binding can be assessed by using modifications of conventional assays that directly measure these biochemical properties. Specifically, DNA-binding activity can be assayed using synthetic DNA oligonucleotides corresponding to Stat3 consensus sequences in the promoters of genes. In vivo screens can be designed to detect disruption of Stat3-specific gene regulation. Specifically, "reporter" sequences that are dependent on Stat3 signaling for expression of proteins that can be conveniently detected based on biochemical properties such as light emission or calorimetric intensity are conveniently used. Another in vivo assay evaluates the effect of compounds on oncogenic properties of human tumor cell lines in culture. The goal of such screens is to identify compounds that effectively stimulate antitumor immunity with minimal toxicity toward normal cells.

In some embodiments, the Stat3 inhibitor may comprise a nucleotide or ribonucleotide sequence, including, but not limited to a Stat3 antisense oligonucleotide (for example, as taught in Wang et al., Nature Medicine 10:1 48-54 (2004), incorporated herein by reference) or interfering RNA. Stat-3 antisense sequences complementary to coding or non-coding regions may be used. Representative Stat3 antisense sequences are taught in U.S. Pat. No. 6,159,694, which is incorporated herein by reference in its entirety. Non-limiting examples of suitable Stat3 antisense sequences include the following:

| Sequence | SEQ ID NO: |
|---|---|
| 5'-ACTCAAACTGCCCTCCTGCT-3' | 1 |
| 5'-TCTGAAGAAACTGCTTGATT-3' | 2 |
| 5'-GCCACAATCCGGGCAATCT-3' | 3 |
| 5'-TGGCTGCAGTCTGTAGAAGG-3' | 4 |
| 5'-TTTCTGTTCTAGATCCTGCA-3' | 5 |
| 5'-TAGTTGAAATCAAAGTCATC-3' | 6 |
| 5'-TTCCATTCAGATCTTGCATG-3' | 7 |
| 5'-TCTGTTCCAGCTGCTGCATC-3' | 8 |
| 5'-TCACTCACGATGCTTCTCCG-3' | 9 |
| 5'-GAGTTTTCTGCACGTACTCC-3' | 10 |

Alternatively, a double-stranded oligonucleotide decoy for the consensus sequence of Stat3 may be employed as a Stat3 inhibitor. Such a decoy suitably closely corresponds to the response element within the promoter region of a Stat3 responsive gene, thereby impairing the authentic interaction.

Interfering RNA (RNAi) may also be used to inhibit Stat3 in an immune cell. Such techniques, also known in the art as post-transcriptional gene silencing, are well known. Suitably, double-stranded RNA corresponding to Stat3 mRNA is used to suppress expression of Stat3 monomers.

It is to be understood that the nucleotide or ribonucleotide sequences used to inhibit Stat3 in an immune cell may be single- or double-stranded. Such sequences may suitably be modified at the base moiety, sugar moiety or phosphate backbone, for example, to improve, e.g., stability or hybridization of the sequences. The nucleotide or ribonucleotide sequences are suitably conjugated to a moiety that will facilitate targeting to, and uptake by, an immune cell. The nucleotide or ribonucleotide sequences are suitably introduced into immune cells using standard molecular biological techniques well known in the art, such as, e.g., using a suitable plasmid or viral vector.

Additional inhibitors of Stat3 signaling which are suitably employed in the present methods include anti-Stat3 antibodies, dominant negative mutants of Stat3, e.g., Stat3β (Nakajima K et al. EMBO J. 15, 3651-3658 (1996), incorporated herein by reference) and inhibitors of upstream kinases, e.g., Janus kinases, Src and BCR-Abl tyrosine kinases. One suitable tyrosine kinase inhibitor is AG-490, as well as related compounds as described in International Application Publication WO 00/44774, incorporated herein by reference in its entirety. Further suitable Stat3 inhibitors include phosphotyrosyl peptides that complex with Stat3 monomers and prevent the formation of dimers, e.g., PY*LKTK (where Y* represents phosphotyrosine) (as taught by Turkson et al., J. Biol. Chem. 276, 45443-45455 (2001), incorporated herein by reference in its entirety).

In some embodiments of the present methods, an immune cell is contacted with the Stat3 inhibitor in vitro, ex vivo or in vivo. For in vivo methods, the Stat3 inhibitor is targeted to the immune cell in a composition that is suitably formulated for systemic administration. One particularly suitable means for targeting a Stat3 inhibitor to an immune cell in vivo is to conjugate the Stat3 inhibitor to an antibody specific for a surface marker of the immune cell of interest. Conjugating antibodies to particular agents is suitably accomplished according to art-recognized methods, e.g., as in U.S. Pat. Nos. 3,927,193, 4,331,647, 4,348,376, 4,361,544, 4,468,457, 4,444,744, 4,460,459, 4,460,561, 4,624,846 and 4,818,709, the disclosures which are incorporated herein by reference. As will be appreciated, multiple immune cell types can be simultaneously targeted with Stat3 inhibitors to provide a multicomponent antitumor immune response. Antibodies are suitably conjugated to particulate drug carriers such as liposomes and microspheres comprising the Stat3 inhibitor.

Surface markers suitably employed to target Stat3 inhibitors to dendritic cells include, but are not limited to, Gr1, VEGF-R, CD1, CD23, CD39, CD40, CD83 and CD146. Surface markers suitably employed to target Stat3 inhibitors to T cells include, but are not limited to CD3, CD4, CD8, CD25 and Lag-3. Surface markers suitably employed to target Stat3 inhibitors to neutrophils include, but are not limited to CD15, CD16, CDw17, CD35, CD66a, CD66c, CD66d, CD68, CD89, CDw92, CD93, CD116, CDw128 and CD156. Surface markers suitably employed to target Stat3 inhibitors to NK cells include, but are not limited to CD2, CD16, CD39, CD56, CD57, CD62L, CD69, CD94, CD98, CD159a, CD161, CD162R, CD165 and CD166. As will be understood, surface markers present on multiple immune cell types may suitably be employed to target Stat3 inhibitors to multiple cell types using antibodies directed to those surface markers. Combinations of antibodies are also suitably employed to target single or multiple immune cell subsets.

A further suitable means known in the art by which Stat3 inhibitors may be targeted to immune cells includes nanoparticle delivery, including aptamer-conjugated nanoparticle delivery.

As an alternative to in vivo targeting of Stat3 inhibitors to immune cells, ex vivo approaches are also suitable for enhancing antitumor activity of immune cells. Suitably, adoptive immunotherapy techniques may be used, wherein immune cells are isolated using techniques known in the art, contacted with a Stat3 inhibitor and then administered to a subject bearing a tumor. Suitably, the immune cells are administered intravenously using conventional methods known in the art.

Additional embodiments of the present invention are directed to a method of killing a tumor cell or inhibiting tumor growth in a subject comprising contacting an immune cell of the subject with a Stat3 inhibitor. In these embodiments, the amount of Stat3 inhibitor suitably administered is a therapeutically effective amount, i.e., an amount sufficient to achieve anti-tumor therapeutic efficacy.

Therapeutic administration of Stat3 inhibitors can be accomplished by any suitable technique presently or prospectively utilized by those skilled in the art. Stat3 inhibitors may be administered by any suitable route known in the art including, for example, oral, nasal, rectal, and parenteral routes of administration. As used herein, the term parenteral includes subcutaneous, intradermal, intravenous, intramuscular, intraperitoneal, and intravenous administration, such as by injection.

Administration of Stat3 inhibitors can be continuous or at intervals as can be readily determined by a person skilled in the art. An ordinarily skilled clinician can determine effective dosages. The specific therapeutically effective dose level for any particular patient will depend upon a variety of factors, including the disorder being treated and the severity of the disorder; activity of the specific compound employed; the specific composition employed; the age, body weight, general health, sex and diet of the patient; route of administration; the rate of excretion of the Stat3 inhibitor employed; the duration of the treatment; drugs used in combination or coincidental with the Stat3 inhibitor and like factors well known in the medical arts. For example, it is well within the level of ordinary skill in the art to start doses of the compound at levels lower than those required to achieve the desired therapeutic effect and to gradually increase the dosage until the desired effect is achieved.

If desired, the effective daily dose may be divided into multiple doses for purposes of administration. Consequently, single dose compositions may contain such amounts or submultiples thereof to make up the daily dose. As noted, those of ordinary skill in the art will readily optimize effective doses and co-administration regimens as determined by good medical practice and the clinical condition of the individual patient. For example, suitable total daily dosages of compositions including CPA-7 may provide about 1 mg/kg to about 10 mg/kg, about 4 mg/kg to about 6 mg/kg, and/or about 5 mg/kg. Doses are suitably administered about twice or about three times per week. Daily administration of lower dosages is also contemplated. Administration is suitably continued until tumor burden is reduced in a subject by at least 50%. Most suitably, administration is continued until tumor is no longer detected in a patient, i.e., the patient is in complete clinical remission.

Compounds useful in the methods of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive platinum complex is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. Compositions including Stat3 inhibitors also preferably include conventional pharmaceutically acceptable excipients which are known to those skilled in the art. Examples of excipients for use with Stat3 inhibitors include ethanol, dimethyl sulfoxide, glycerol, alumina, starch, and equivalent carriers and diluents. To provide for the administration of such dosages for the desired therapeutic application, pharmaceutical compositions of the invention will advantageously comprise between about 0.1% and 99%, and especially, 1 and 15% by weight of the total of one or more of the Stat3 inhibitors based on the weight of the total composition including carrier or diluent.

In certain embodiments of the invention, killing a tumor cell or inhibiting tumor growth in a subject comprises contacting an immune cell, such as a bone marrow cell, with a Stat3 inhibitor. The immune cells may be isolated from the patient bearing the tumor (autologous bone marrow transplant) or may be isolated from a donor (heterologous bone marrow transplant), taking into consideration all relevant factors, such as donor compatibility. Methods of isolating immune cells or subsets of immune cells from the bone marrow of a patient are known in the art and suitably employed with the present invention. After isolation, the immune cells or subsets of immune cells from the bone marrow are contacted with a Stat3 inhibitor or combination of Stat3 inhibitors ex vivo. For example, immune cells may be contacted with CPA-7 at a concentration of 10 μm for about 8 hours. After sufficient incubation with a Stat3 inhibitor, e.g., until antitumor function is enhanced in comparison to control cells, the immune cells are intravenously infused or otherwise administered to the subject or patient bearing the tumor.

In other embodiments of the invention, killing a tumor cell or inhibiting tumor growth in a subject comprises contacting a tumor-infiltrating lymphocyte (TIL) with a Stat3 inhibitor. Methods of isolating TILs are known in the art. Isolated TILs may be contacted with a Stat3 inhibitor as described above and administered to the subject bearing the tumor to be treated.

The present methods are suitably employed in combination with at least one further anti-hyperproliferative therapy. Such further therapies may be termed "adjunct" therapies. One suitable adjunct therapy for use with methods of inhibiting Stat3 in an immune cell includes administration of a chemotherapeutic agent to the subject. Most chemotherapeutic agents fall into the following categories: alkylating agents, antimetabolites, antitumor antibiotics, corticosteroid hormones, mitotic inhibitors, and nitrosoureas. Any combination of specific chemotherapeutic agents may be used in connection with the present methods. It is envisioned that lower dosages of chemotherapeutic agents may be employed when used in combination with the present methods than are typically used in monotherapy.

Similarly, the present methods may be suitably employed in combination with administration of a tumor-specific vaccine to the subject. Suitable tumor specific vaccines may comprise killed tumor cells displaying a protein associated with a particular tumor that have been shown to provoke an immune response to the tumor. DNA vaccines are also known and are suitably used in connection with the presently described methods. Administration and dosage considerations are within the skill in the art.

The present methods are also suitably employed in combination with radiation therapy, as conventionally employed in the art. Radiation may be administered externally or internally using conventional radiation dosing schedules. For example, radiation therapy may be given daily, 5 days per week. Radiation dosage depends on a number of factors including tumor type, age, weight and condition of the patient, as well as other factors typically considered by the skilled clinician. The typical dose for a solid epithelial tumor may range from 50 to 70 grays (Gy) or more, while lymphomas (white cell) tumors might receive doses closer to 20 to 40 Gy given in daily doses. The total dose can be given in daily fractions using external beam radiation or the total dose can be given via other methods such as implants that deliver radiation continuously over a given timeframe. Depending on the implant type, it may be given as a fraction (e.g. High Dose Rate HDR) over minutes or hours. Alternatively, permanent seeds may be implanted (such as in the prostate) which slowly deliver radiation until the seeds become inactive. As with chemotherapy, it is envisioned that lower dosages of radiation may be employed when used in combination with the present methods than are typically used in monotherapy.

The following examples are provided to assist in a further understanding of the invention. The particular materials and conditions employed are intended to be further illustrative of the invention and are not limiting upon the reasonable scope thereof.

Example 1

Materials and Methods

The following materials and methods were used in the experiments described in Examples 2-7.

Cell lines. Mouse B16 melanoma, YAC-1 and P815 target cells were purchased from American Type Culture Collection. MB49 bladder carcinoma and C4 mouse melanoma lines were gifts from T. Ratliff (University of Iowa) and J. Fidler (M.D. Anderson Cancer Center), respectively.

In vivo experiments. Mouse care and experimental procedures were performed under pathogen-free conditions in accordance with established institutional guidance and approved protocols from Institutional Animal Care and Use Committees of the University of South Florida and Johns Hopkins University. Mx1-Cre mice were obtained from the Jackson Laboratory and Stat3$^{loxP/loxP}$ mice were obtained from S. Akira and K. Takeda (Osaka University). Generation of mice with Stat3$^{-/-}$ hematopoietic cells by an inducible Mx1-Cre recombinase system was performed as described by Lee C K et al., *Immunity* 17, 63-72 (2002) and Alonzi T et al., *Cytokine* 26, 45-56 (2004), each of which are specifically incorporated herein by reference. Deletion of Stat3 was verified by PCR, using primer sets that distinguish Stat3, Stat3$^{loxP}$ and Stat3-deleted alleles, and by EMSA.

For EMSA, nuclear extracts were prepared from Stat3$^{+/+}$ and Stat3$^{-/-}$ bone marrow cells stimulated for 20 minutes with IL-10 (10 ng/ml) and/or GM-CSF (20 ng/ml). Bone marrow transplantations were performed with whole bone marrow obtained from Stat3$^{+/+}$ and Stat3$^{-/-}$ donor mice as described by Wang, J. W. et al., *Science* 295, 2094-2097 (2002), which is incorporated herein by reference.

For subcutaneous tumor challenge, 5×10$^4$ B16 or 5×10$^5$ MB49 tumor cells were injected into 7-8-week-old wild-type mice at 5 days after poly(I:C) treatment, or 2 months after bone marrow transplant. After 3-5 weeks, mice were killed and spleens as well as tumor specimens were harvested.

For therapeutic studies, Stat3$^{loxP/loxP}$ or Cre-Stat3$^{loxP/loxP}$ mice were challenged with either B16 or MB49 tumor cells, followed by poly(I:C) treatments when tumors were at least 3-5 mm in diameter. Because of a male antigen-specific response in female mice by tumor challenge, MB49 tumor experiments were carried out using male mice only.

For CPA-7 treatment, MB49 tumors were implanted into male C57BL/6 mice and tumors were allowed to grow until 5-7 mm in diameter. Mice were given intravenous injections of either vehicle (10% DMSO/PBS) or 5 mg/kg CPA-7 once every 3 days.

Flow cytometry. Single-cell suspensions were prepared by mechanic dispersion of spleen or tumor tissues. 1×10$^6$ freshly prepared cells suspended in a mixture of PBS, 2% FCS and 0.1% (wt/vol) sodium azide were preincubated with FcγIII/IIR-specific antibody to block nonspecific binding and cells were stained with different combinations of fluorochrome-coupled antibodies to CD11c, I-A$^b$ (MHC class II), CD86, CD11b, Gr1, CD49b, CD3, CD25 or Lag-3, or with annexin V (BD Biosciences). Fluorescence data was collected on FACSCalibur (Beckton Dickinson) and analyzed using FlowJo software (Tree Star).

Isolation of tumor-infiltrating immune cell subsets and intracellular staining of signaling molecules. Freshly excised tumor tissues were gently minced into small pieces and incubated in 400 U/ml of collagenase D (Roche) solution for 30 minutes at 37° C. Cell suspensions were filtered through a mesh filter for isolation of various immune cell subsets using specific antibodies in combination with EASYSEP magnetic nanoparticles (StemCell Technologies, Canada). Isolated tumor-infiltrating cells were fixed in paraformaldehyde and permeated in methanol before intracellular staining with antibodies to phosphotyrosine-Stat3 and Stat1 (BD Biosciences) or with Foxp3-specific antibody (eBiosciences). Fluorescence data was collected on FACSCalibur (Beckton Dickinson) and analyzed using FlowJo software (Tree Star).

Isolation and functional analysis of splenic DCs. DCs were isolated from mouse spleens and purified using CD11c MACS beads (Miltenyi Biotec). For IL-12 measurement by ELISA (Endogen), DCs were cultured with 100 ng/ml lipopolysaccharide for 18 hours to collect supernatants. A T-cell proliferation assay with CD4$^+$ T cells purified from OTII mice was performed as described by Wang, T. et al., *Nat. Med.* 10, 48-54 (2004), which is incorporated herein by reference.

Immunohistochemistry. Five millimeter sections of flash-frozen tumor specimens were fixed in acetone, stained with antibodies to CD4 and CD8, and detected with peroxidase- or alkaline phosphatase-coupled secondary antibodies using NovaRED and Blue Chromogen (Vector) as described by Wang, J. W. et al., *Science* 295, 2094-2097 (2002), which is incorporated herein by reference.

Transverse colon sections were stained with hematoxylin-eosin and antibodies to CD4, CD8 or CD11b. Staining with rat IgG was used as a negative control.

Cytotoxicity assays. NK cell and neutrophil cytotoxicity assays were performed as described by Wei, S. et al., *J. Exp. Med.* 187, 1753-1765 (1998), which is incorporated herein by reference. Briefly, a 4-hour $^{51}$Cr-release assay was carried out using YAC-1 cells as targets for enriched NK cells or FcγR$^+$ mouse mastocytoma (P815) cells as targets for enriched neutrophils.

ELISPOT assays. Spleens were harvested from mice challenged subcutaneously with 1×10$^5$ B16 tumor cells 2 weeks post-challenge. 5×10$^5$ splenocytes were seeded into each well of a 96-well filtration plate in the presence or absence of 10 µg/ml of p15E peptide and incubated at 37° C. for 24 hours. Peptide-specific IFN-γ-positive spots were detected according to the manufacturer's protocol (Cell Sciences), and scanned and quantified using the Immunospot Analyzer from Cellular Technology Ltd.

Statistical analysis. To compare tumor size or surface marker expression between multiple test groups in mouse experiments, a one-way ANOVA followed by Newman-Keuls test was performed. An unpaired t-test was used to calculate two-tailed p values to estimate statistical significance of differences between two treatment groups. Statistically significant p values were labeled as follows: *P<0.001; P<0.01 and *P<0.05. Data were analyzed using Prism software (GraphPad).

Example 2

Generation of Stat3$^{-/-}$ Adult Mice

Generation of Stat3$^{-/-}$ mice by an inducible Mx1-Cre recombinase system was performed as described in Example 1. Injection of poly(I:C) into mice carrying the Mx1-Cre transgene (Cre) and Stat3 alleles flanked by loxP sites (Stat3$^{loxP/loxP}$) led to effective Stat3 deletion in bone marrow cells, as determined by PCR analysis of genomic DNA from bone marrow, using primers that distinguish full-length Stat3$^{loxP}$ and Stat3-deleted alleles. Results, shown in FIG. 1, demonstrate effective Stat3 deletion.

Figure 2:
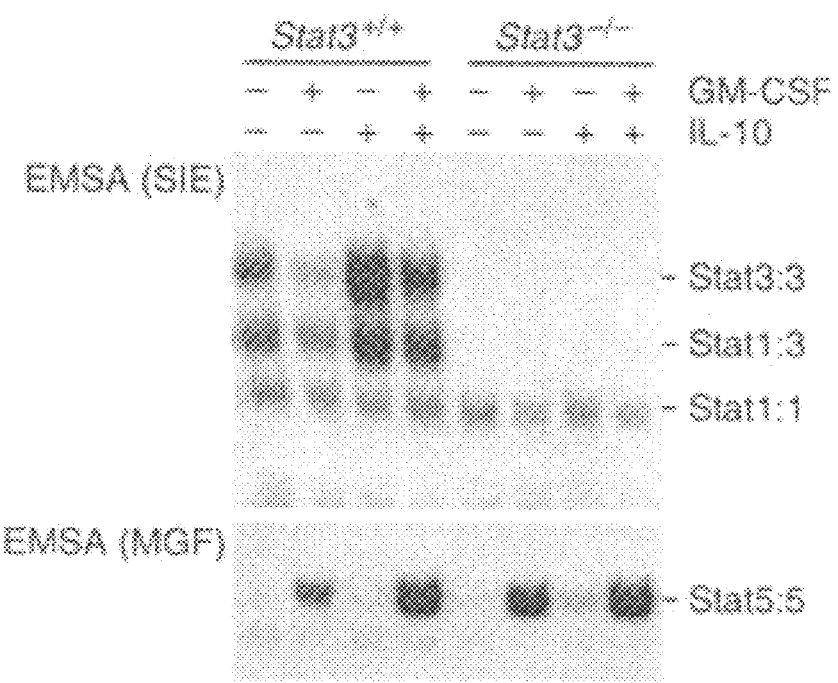
FIG. 2 shows electrophoretic mobility shift assay (EMSA) results confirming lack of Stat3-DNA binding activity in $Stat3^{-/-}$ bone marrow cells. SIE is a DNA probe for detecting Stat3 and Stat1 DNA-binding activity, whereas MGF detects Stat5-DNA binding. Positions of Stat homo- and heterodimers are indicated.

Stat3 deletion was confirmed by an electrophoretic mobility shift assay (EMSA). Nuclear extracts were prepared from Stat3$^{+/+}$ and Stat3$^{-/-}$ bone marrow cells stimulated for 20 minutes with IL-10 (10 ng/ml) and/or GM-CSF (20 ng/ml). Preparations were probed with SIE, which detects Stat1 and Stat3 binding activity, and MGF, which detects Stat-5 binding. FIG. 2 shows lack of Stat3 dimer binding activity in Stat3$^{-/-}$ mice.

Figure 3:
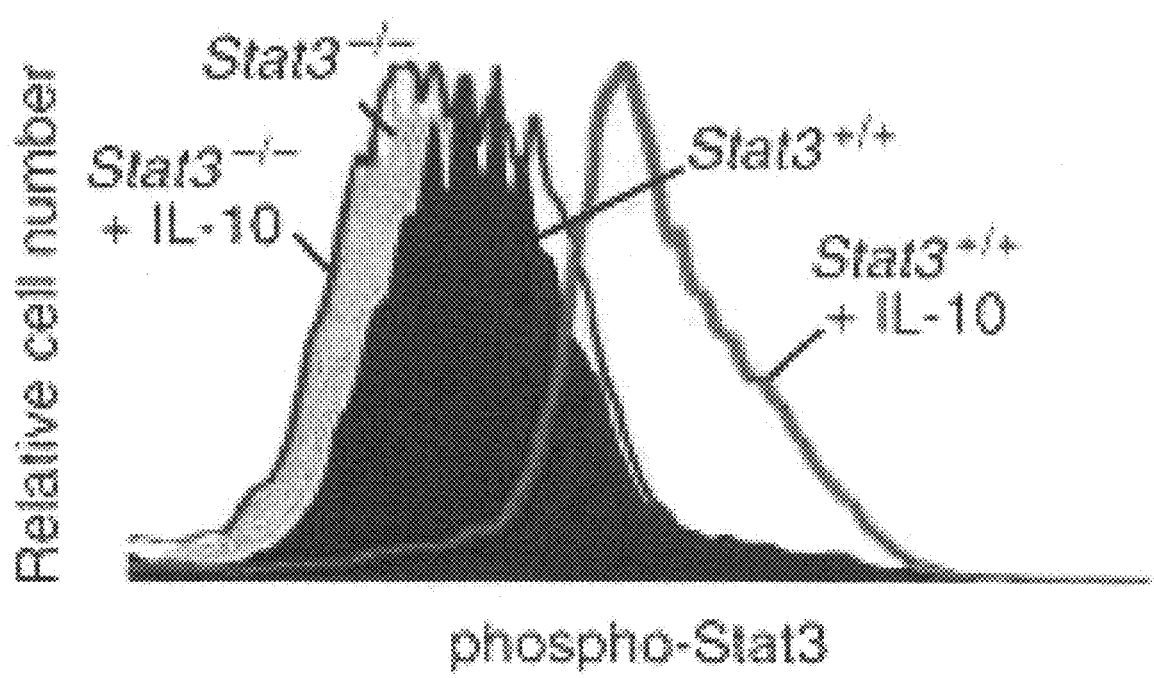
FIG. 3 depicts results of intracellular flow cytometric analysis using an antibody to detect tyrosine-phosphorylated Stat3 (phospho-Stat3).

CD11c$^+$ dendritic cells purified from spleens of Stat3$^{+/+}$ and Stat3$^{-/-}$ mice were stimulated with IL-10, followed by intracellular staining with a phospho-Stat3-specific antibody. Intracellular flow cytometric analysis further confirmed deletion of Stat3 in dendritic cells, as shown in FIG. 3.

Example 3

Stat3 Ablation Activates Dendritic Cells

Figure 4:
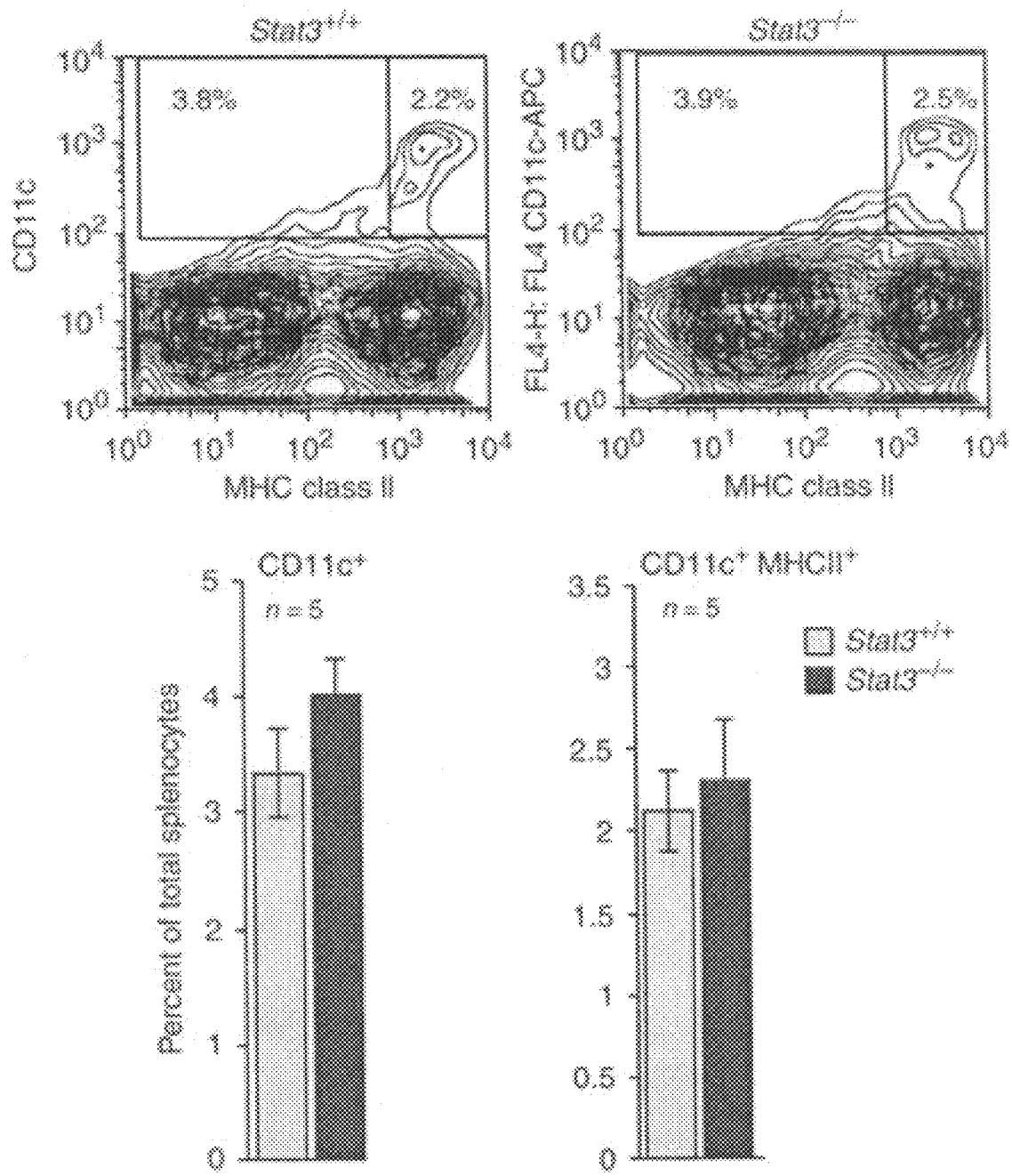
FIG. 4 shows results of flow cytometry analysis of splenic DCs from $Stat3^{-/-}$ and $Stat3^{+/+}$ tumor bearing mice. Top, percentage of total splenocytes of $CD11c^+$ and $CD11c^+MHC$ $II^{+low\ or\ high}$ subsets. Bottom, data from FACS are presented as means±s.d.; n=5.

Splenic DCs were isolated from Stat3$^{+/+}$ and Stat3$^{-/-}$ mice as described in Example 1. 1×10$^6$ freshly prepared cells were suspended in a mixture of PBS, 2% FCS and 0.1% (wt/vol) sodium azide with FcγIII/IIR-specific antibody to block non-specific binding. After staining with fluorochrome-coupled anti-CD11c and anti-I-A$^d$ (MHC class II), flow cytometric analysis showed that the total number of cells is not reduced in Stat3$^{-/-}$ as compared to Stat3$^{+/+}$ mice (FIG. 4).

Figure 5:
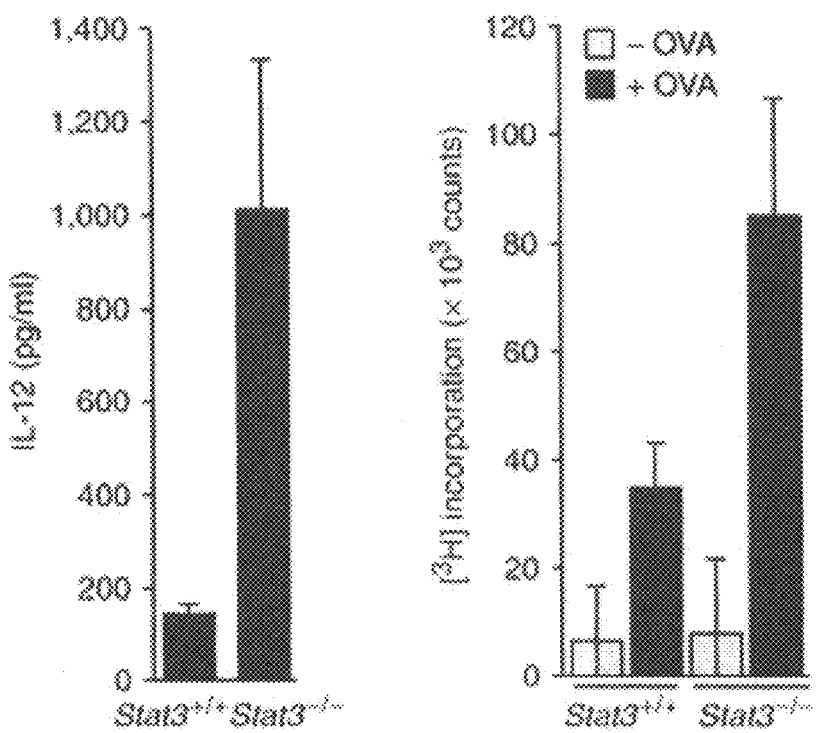
FIG. 5 shows results of an ELISA assay for IL-12 expression by $CD11c^+$ DCs purified from spleens of tumor-bearing $Stat3^{+/+}$ and $Stat3^{-/-}$ mice after lipopolysaccharide stimulation (left panel). Also shown is proliferation of OTII $CD4^+$ T cells stimulated by $Stat3^{+/+}$ and $Stat3^{-/-}$ DCs±OVA (right panel). Data are shown as means±s.d.; n=3.

Next, splenic DCs from tumor-bearing Stat3$^{+/+}$ and Stat3$^{-/-}$ mice were cultured with 100 ng/ml lipopolysaccharide for 18 hours and supernatants were collected. ELISA was used to determine IL-12 levels in the supernatants. As shown in FIG. 5 (right panel), Stat3$^{-/-}$ mice produced higher levels of IL-12. Proliferation of OTII CD4$^+$ T cells after stimulation by splenic DCs (+ or –OVA) from tumor-bearing Stat3$^{+/+}$ and Stat3$^{-/-}$ mice was also measured. The Stat3$^{-/-}$DCs showed enhanced ability to present antigen and activate T cells, as shown in FIG. 5 (left panel).

Figure 6:
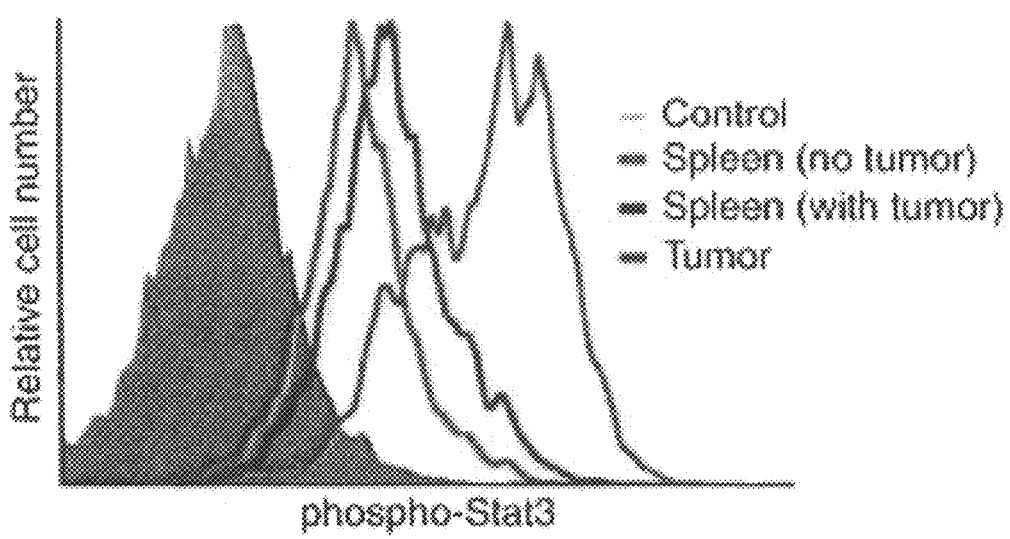
FIG. 6 shows results of intracellular staining of tumor-infiltrating DCs with antibody to phosphorylated Stat3 (phospho-Stat3), followed by flow cytometry. Representative results of three independent experiments with three to four mice per group are shown.
Figure 7:
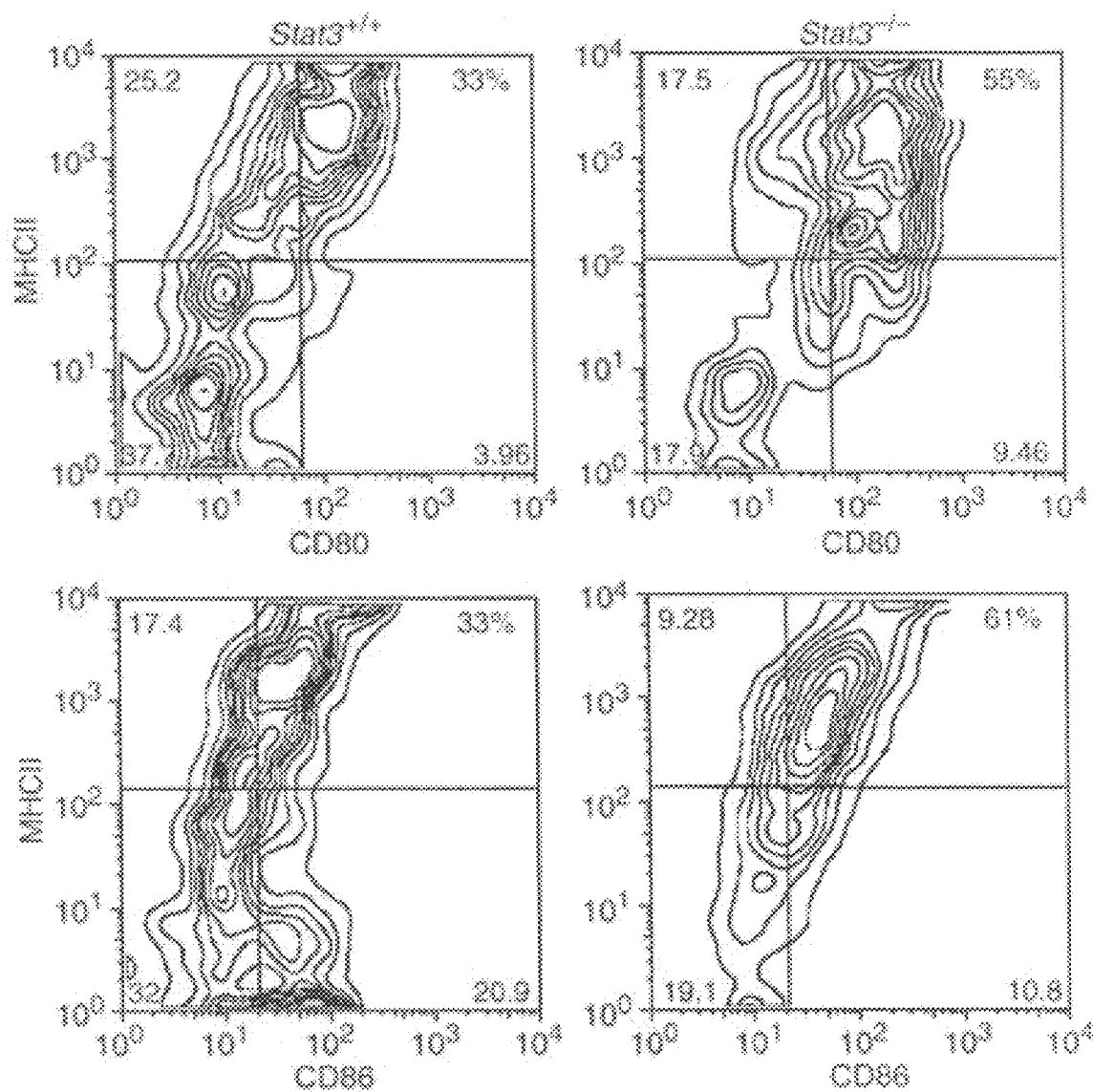
FIG. 7 depicts representative results of FACS analysis of MHCII$^{hi}$CD80$^{hi}$ or MHCII$^{hi}$CD86$^{hi}$ tumor-infiltrating CD11c$^+$ DCs. Shown are data from one of three independent experiments with four to six mice per group.

To evaluate effects of Stat3 deletion on tumor-infiltrating dendritic cells, freshly excised tumor tissue was minced and incubated in 400 U/ml collagenase D (Roche) solution for 30 minutes at 37° C. Cell suspensions were filtered through a mesh filter and magnetic nanoparticles in combination with dendritic cell-specific antibodies (anti-MHC II, CD80, CD86 and CD11c) were used to isolate DCs. Isolated DCs were fixed in paraformaldehyde and permeated in methanol before intracellular staining with antibody to phosphorylated Stat3 and flow cytometric analysis. As shown in FIG. 6, Stat3 is constitutively activated in tumor infiltrating DCs from control mice. Moreover, as shown in FIG. 7, tumor infiltrating DCs from Stat3$^{-/-}$ mice showed increased expression of MHC class II, CD80 and CD86, when compared to Stat3$^{+/+}$ mice.

Figure 8:
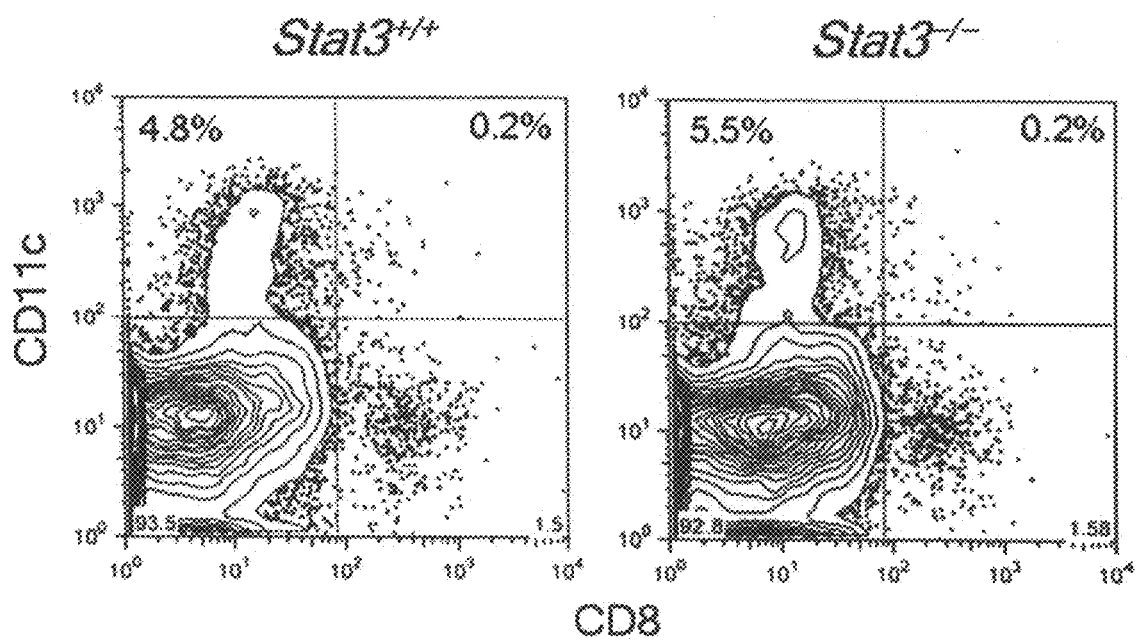
FIG. 8 depicts results of FACS analysis comparing tumor-infiltrating CD8$^+$ and CD8$^-$ DCs in Stat3$^{+/+}$ and Stat3$^{-/-}$ mice. Representative results of three experiments with 3-6 mice per group are shown.
Figure 9:
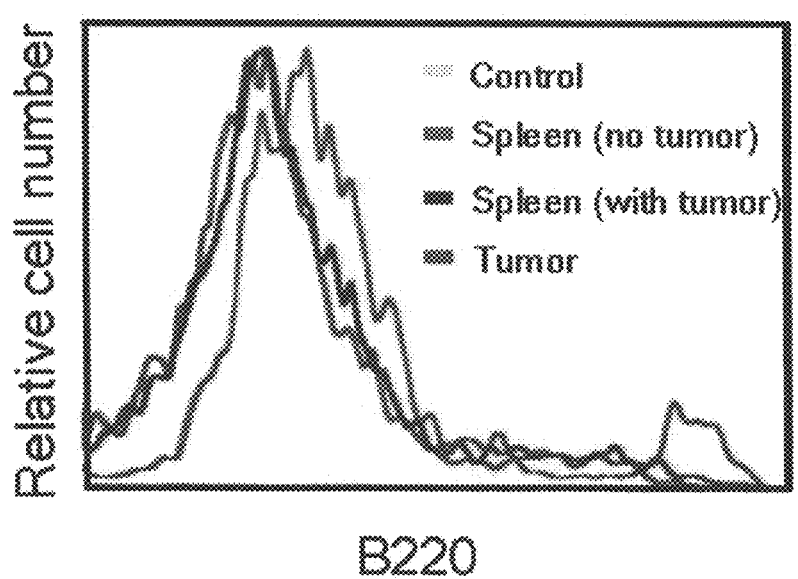
FIG. 9 depicts comparison of splenic cell suspensions prepared from tumor-free and B16 tumor-bearing mice and tumor-infiltrating DCs by flow cytometric analysis.
Figure 10:
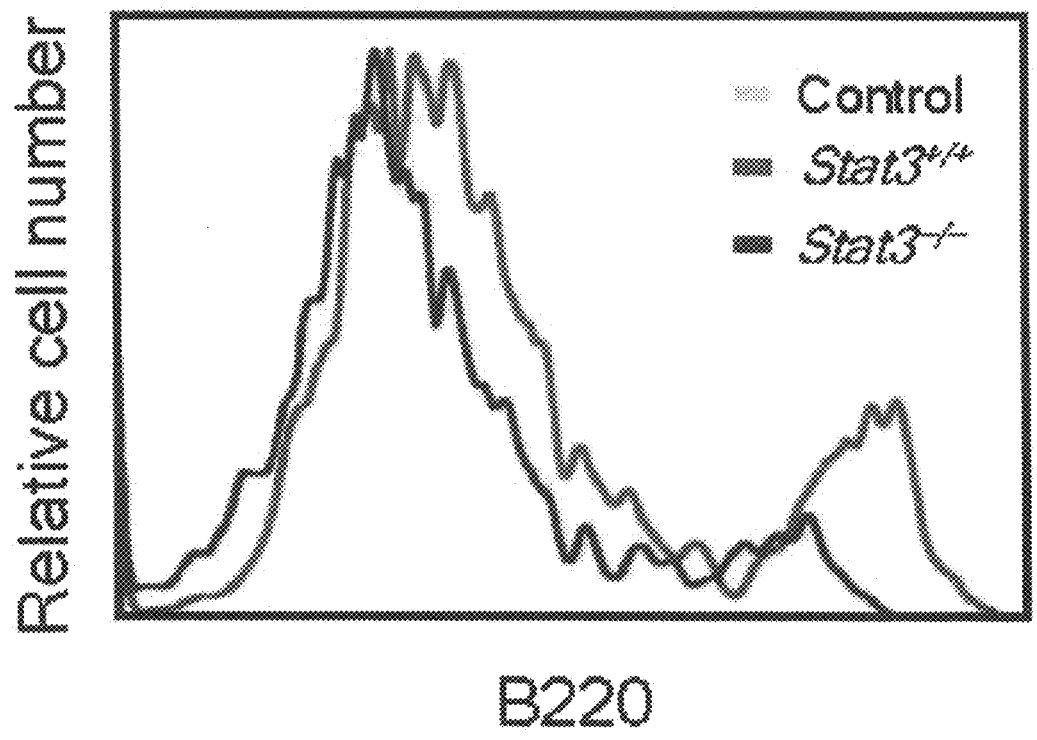
FIG. 10 depicts comparison of tumor-infiltrating DCs from Stat3$^{+/+}$ and Stat3$^{-/-}$ mice by flow cytometric analysis.

Subsets of tumor-infiltrating DCs in both Stat3$^{+/+}$ and Stat3$^{-/-}$ mice were further analyzed for CD11c and CD8 expression. Results, shown in FIG. 8, indicate that tumor-infiltrating DCs were essentially all CD8$^-$ in both Stat3$^{+/+}$ and Stat3$^{-/-}$ mice. Cell suspensions from spleens of tumor-free and B16 tumor-bearing mice were stained for CD11c and B220 and compared with tumor-infiltrating DCs by flow cytometric analysis. As shown in FIGS. 9 and 10, the percentage of B220$^+$ plasmacytoid DCs was higher in tumor than in spleen, and a decrease in tumor-infiltrating B220$^+$ plasmacytoid DCs (thought to be involved in tolerogenic functions through generation of regulatory T cells) in Stat3$^{-/-}$ mice was detected.

Example 4

Stat3 Ablation Activates Neutrophils and NK Cells

Figure 11:
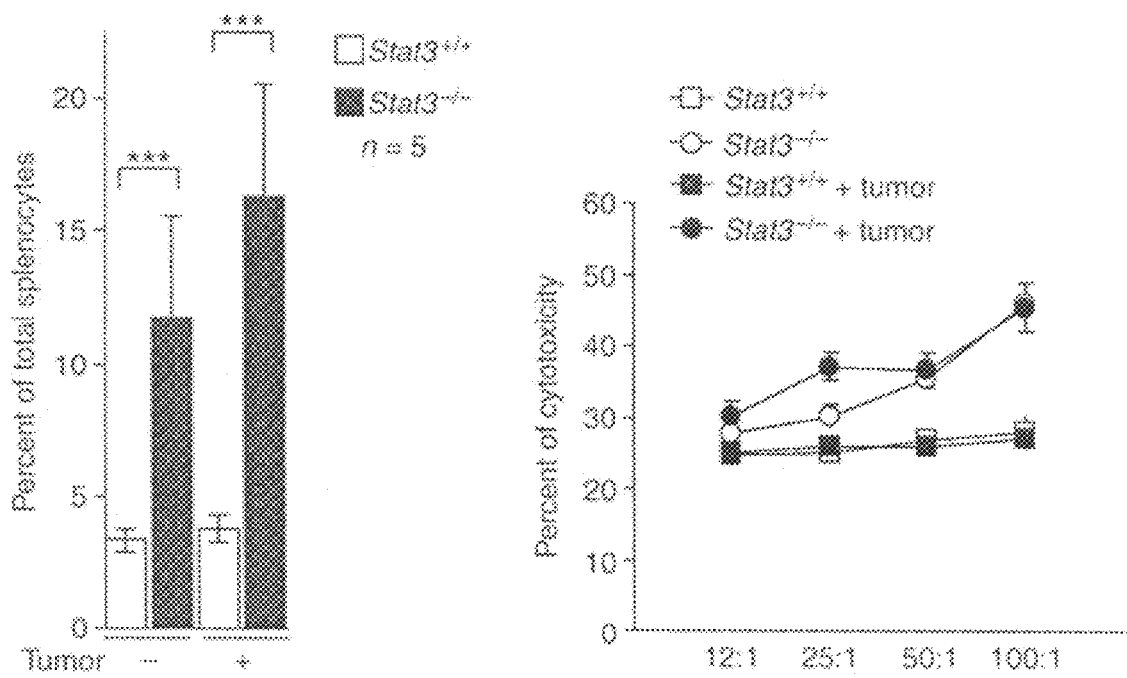
FIG. 11 is a graphical representation of the percentage of splenic neutrophils (Gr1$^+$CD11b$^+$) from B16 tumor-bearing and tumor-free Stat3$^{+/+}$ and Stat3$^{-/-}$ mice as determined by FACS analysis (left). Shown are the means±s.d.; n=5. ***P<0.001. Also shown are results of a $^{51}$Cr-release assay to determine cytotoxicity of neutrophils using FcγR$^+$ mouse mastocytoma (P815) cells as targets (right). Shown are representative results from one of three independent experiments done in triplicate; means±SD. Two mice were used for each experiment.

Stat3$^{+/+}$ and Stat3$^{-/-}$ mice were challenged subcutaneously with 5×10$^4$ B16 tumor cells as described in Example 1. After 3-5 weeks, tumor-challenged and control mice were killed and spleens were harvested. Total spenocytes were analyzed by FACS to determine the percentage of neutrophils (Gr1$^+$ CD11b$^+$) present. As shown in FIG. 11 (left panel), induction of Stat3 deletion considerably increased the number of splenic granulocytic lineage cells. A $^{51}$Cr-release assay was conducted to assess cytolytic activity of isolated neutrophils, using FcγR$^+$ mouse mastocytoma (P815) cells as targets. As shown in FIG. 11 (right panel), the results demonstrate that reduced Stat3 signaling in neutrophils enhances their cytolytic activity against target tumor cells, regardless of whether they were isolated from tumor-free or tumor-bearing mice.

Figure 12:
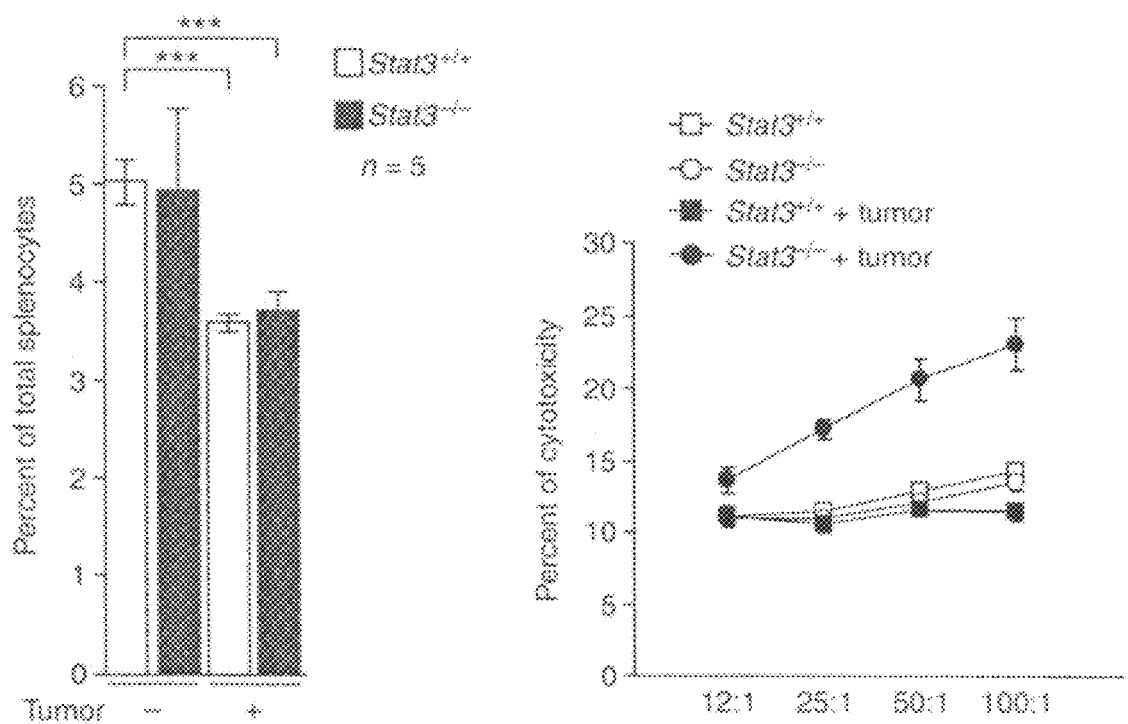
FIG. 12 is a graphical representation of the percentage of splenic NK cells from Stat3$^{+/+}$ and Stat3$^{-/-}$ mice with and without B16 tumor as determined by FACS analysis using CD49b-specific antibody (left). Shown are the means±s.d.; n=5. ***P<0.001. Also shown are results of a $^{51}$Cr-release assay to assess NK cell cytotoxicity using YAC-1 cells as targets (right). Shown are the representative results from one of three independent experiments done in triplicate.

Splenocytes isolated from tumor-challenged and control Stat3$^{+/+}$ and Stat3$^{-/-}$ mice were also analyzed by FACS to determine the percentage of NK cells (CD49b$^+$). As shown in FIG. 12 (left panel), there was no significant change in the number of NK cells between Stat3$^{+/+}$ and hematopoietically Stat3-ablated mice. However, in the presence of tumor, NK cell numbers were decreased by about 25% in both groups. Splenic NK cytolytic activity was assessed using a $^{51}$Cr-release assay with YAC-1 cells as targets. As shown in FIG. 12 (right panel), the cytolytic activity of NK cells isolated from tumor-free mice did not differ between Stat3$^{-/-}$ and Stat3$^{+/+}$ mice. However, after tumor challenge, NK cells from Stat3$^{-/-}$ mice showed enhanced cytolytic activity against target cells.

Figure 13:
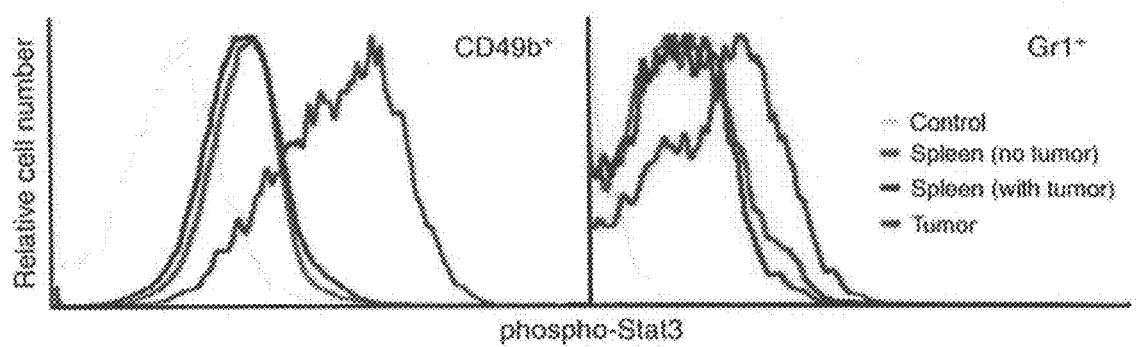
FIG. 13 is a graphical representation of the results of FACS analyses of tumor-infiltrating NK cells (CD49b$^+$) and granulocytes (Gr1$^+$) from wild-type mice with antibody to phospho-Stat3.

Tumor-infiltrating NK cells and neutrophils from wild-type mice were evaluated for phosphorylation by intracellular staining with antibody to phospho-Stat3 followed by FACS analysis. The results, shown in FIG. 13, show that Stat3 was constitutively activated in tumor-infiltrating NK cells and neutrophils, as compared with their splenic counterparts.

Figure 14:
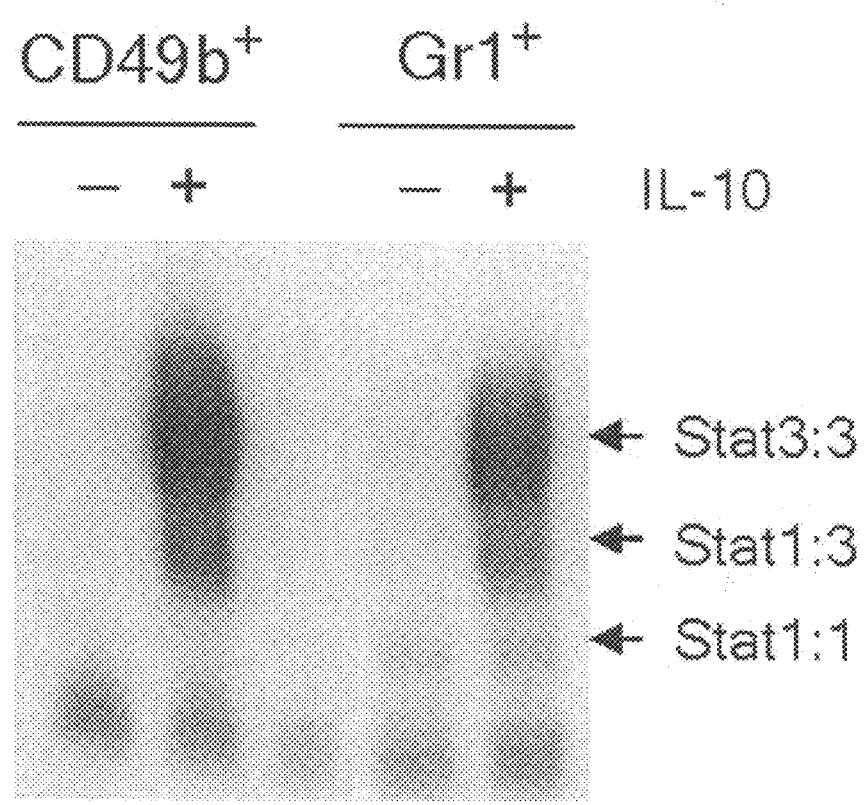
FIG. 14 depicts the results of EMSA analysis of splenic NK cell and granulocyte nuclear extracts incubated with and without IL-10 and probed for Stat heterodimers with SIE.
Figure 15:
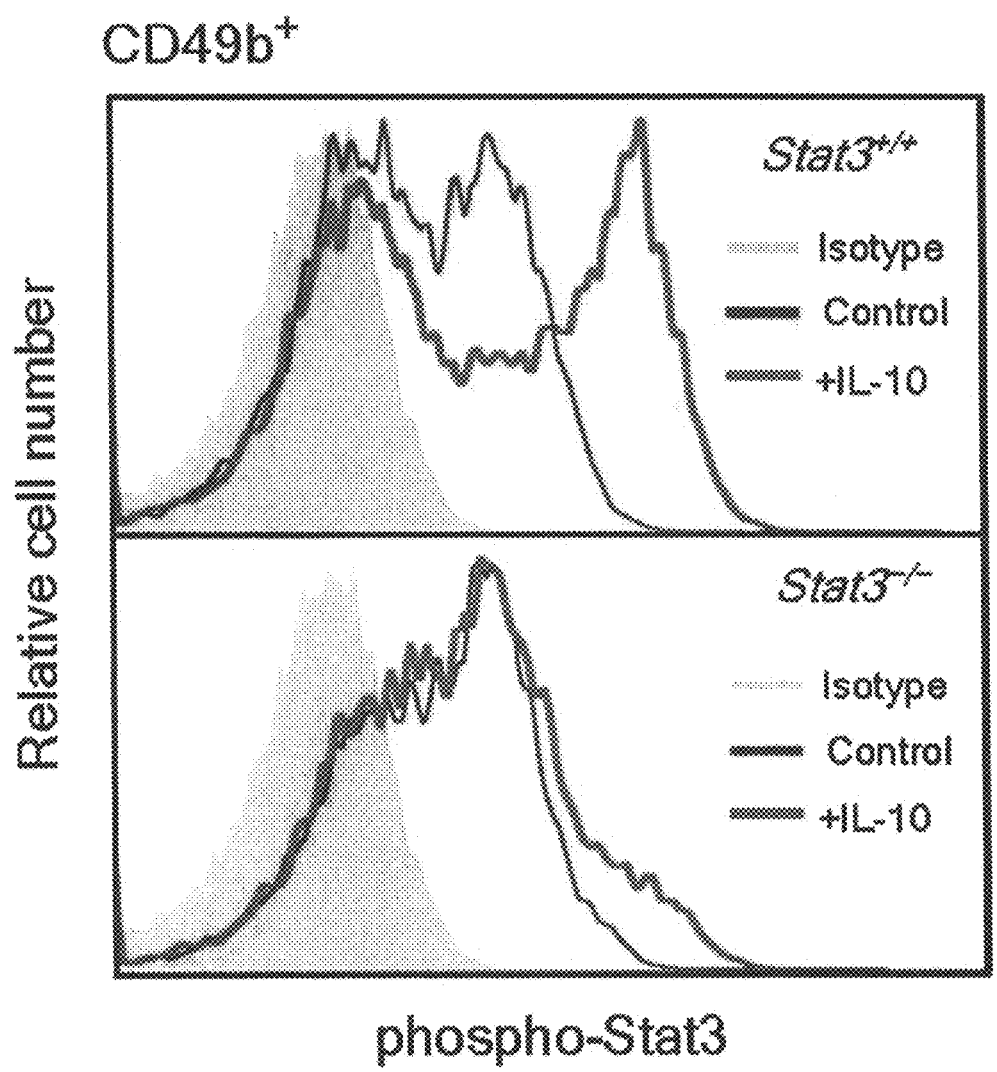
FIG. 15 depicts FACS analysis of Stat3$^{+/+}$ and Stat3$^{-/-}$ splenic NK cells using anti-phospho-Stat3 antibody to assess activation; isotype indicates stating with isotype antibody; control indicates untreated cells; +IL-10 indicates cells were stimulated with 20 ng/ml IL-10 for 20 minutes.
Figure 16:
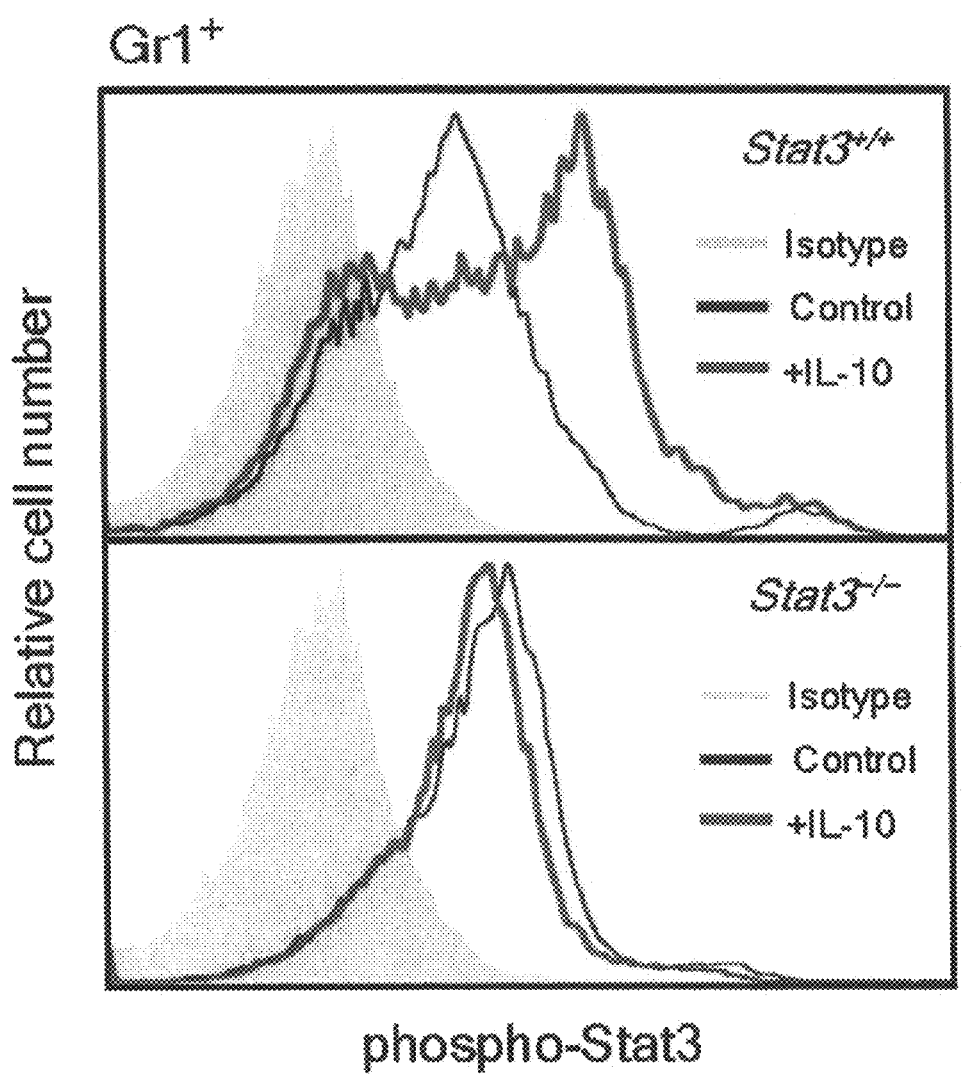
FIG. 16 depicts FACS analysis of Stat3$^{+/+}$ and Stat3$^{-/-}$ splenic granulocytes using anti-phospho-Stat 3 antibody to assess activation; isotype indicates stating with isotype antibody; control indicates untreated cells; +IL-10 indicates cells were stimulated with 20 ng/ml IL-10 for 20 minutes.

Nuclear extracts were prepared from neutrophils and NK cells isolated from spleens of tumor-bearing mice and incubated with or without IL-10 (20 ng/ml for 20 minutes). Flow cytometry and electrophoretic mobility shift assay (EMSA) indicated that IL-10 activates Stat3 in NK cells (CD49b$^+$ CD3$^-$) and granulocytes (Gr1$^+$), as shown in FIGS. 14-16.

Figure 17:
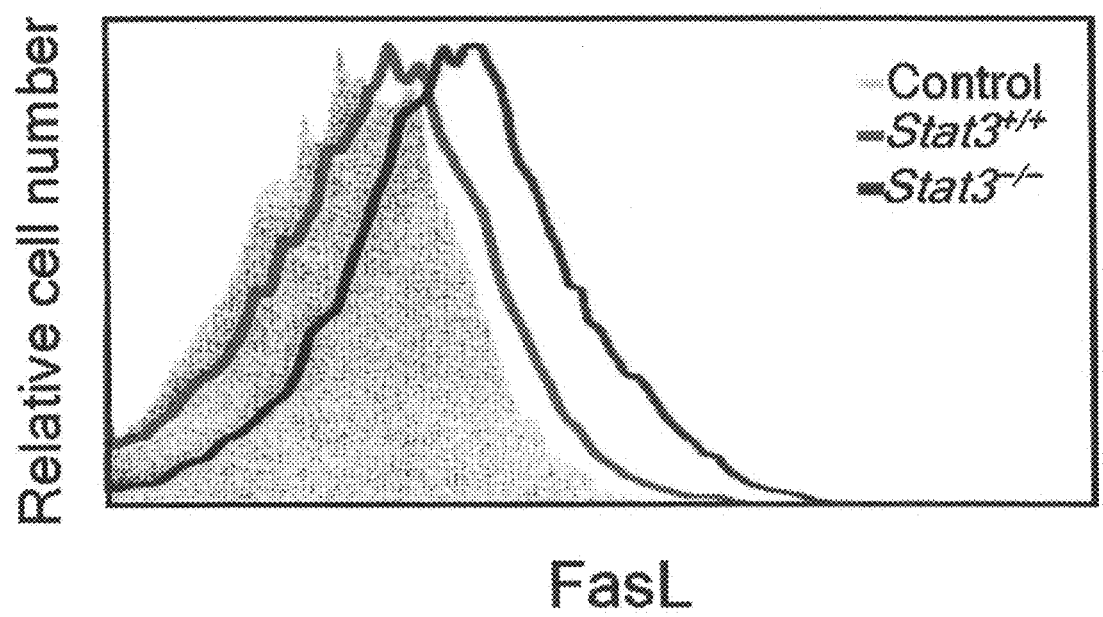
FIG. 17 depicts FACS analysis for FasL expression in Stat3$^{+/+}$ and Stat3$^{-/-}$ tumor-infiltrating neutrophils from B16 tumor-bearing mice.

Next, neutrophils from B16-tumor bearing mice were analyzed for FasL expression three weeks after tumor challenge. As shown in FIG. 17, FasL expression was increased in Stat3$^{-/-}$ Gr1$^+$CD11b$^+$ neutrophils.

Example 5

Stat3 Ablation Activates T-Cells

Percentage of T cells (CD3$^+$) in spleens of tumor-free and B16 tumor-bearing mice with and without Stat3 was assessed by flow cytometry. Although ablation of Stat3 alleles in bone marrow cells led to a reduction of absolute numbers of T cells in tumor-free mice, as shown in FIG. 18, no difference was observed in the numbers of T cells in the tumor-bearing Stat3$^{+/+}$ versus Stat3$^{-/-}$ mice. As shown in FIG. 19, T cells from B16 tumor-bearing mice with Stat3$^{-/-}$ hematopoietic cells were able to mount stronger responses against an endogenous B16 tumor antigen than their Stat3$^{+/+}$ counterparts, as assessed by IFN-γ ELISPOT.

Figure 21:
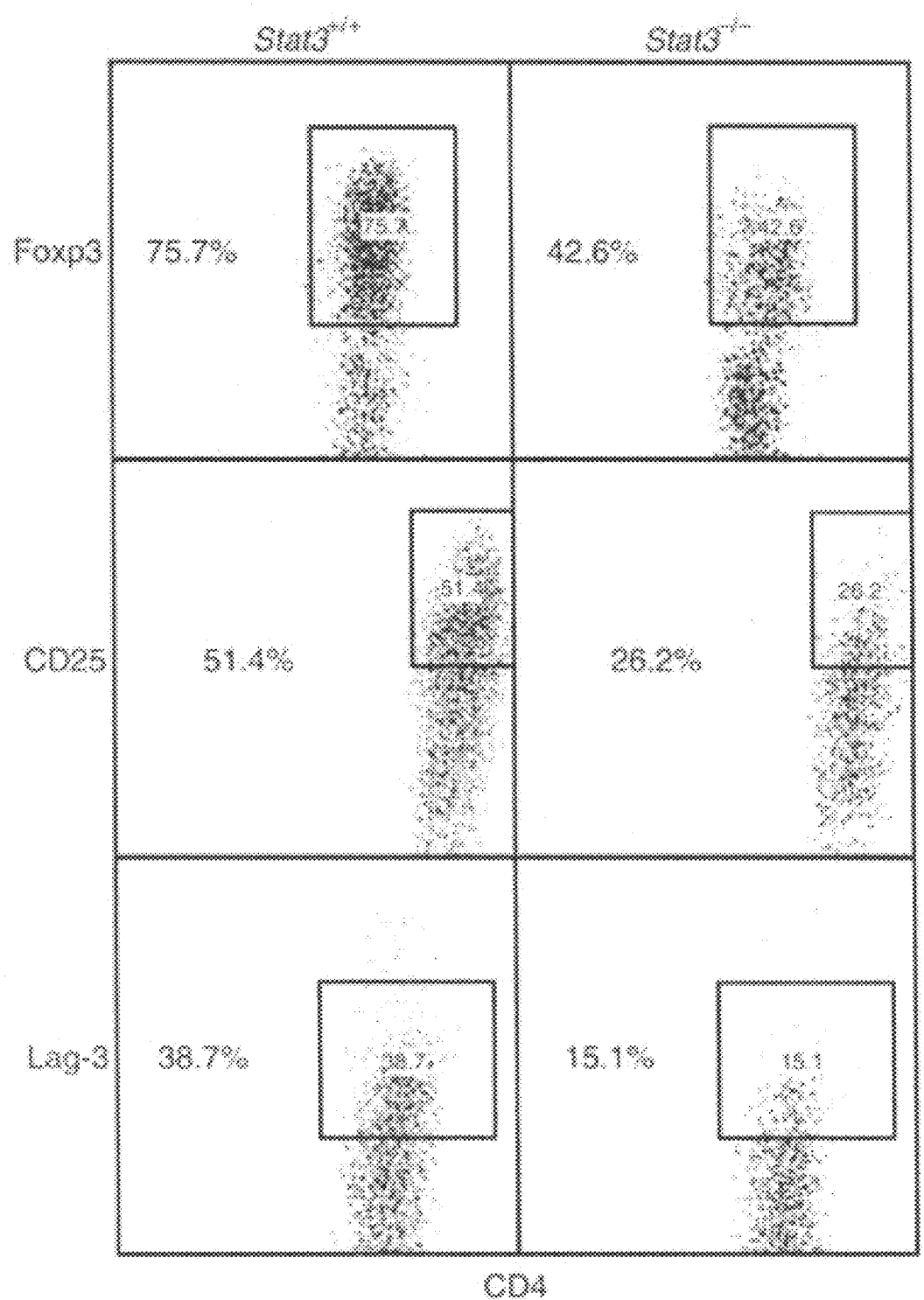
FIG. 21 depicts results of flow cytometry analysis for surface expression of CD25 and Lag-3 or intracellular levels of Foxp3 in tumor-infiltrating T$_{reg}$ cells from Stat3$^{+/+}$ and Stat3$^{-/-}$ mice. Shown are percentages of double-positive cells, representative of three independent experiments.

Because the ability of T cells to infiltrate tumors is considered crucial for induction of tumor regression, T cells from Stat3$^{-/-}$ mice were examined for ability to infiltrate tumors. Immunohistochemical staining of B16 and MB49 mouse tumors showed considerably higher infiltration by T lymphocytes in tumor tissues from Stat3$^{-/-}$ mice. As shown in FIG. 20, immunohistochemical analysis of B16 (top) and MB49 (bottom) tumor tissue sections prepared from Stat3$^{+/+}$ and Stat3$^{-/-}$ mice demonstrated that T cells in mice with Stat3$^{-/-}$ hematopoietic cells infiltrate tumors more efficiently. As eradication of tumors, including B16 tumors, is thought to be inhibited by T regulatory (T$_{reg}$) cells, the effect of Stat3 deficiency in hematopoietic cells on tumor-infiltrating T$_{reg}$ cells was also determined. As shown in FIG. 21, the proportions of tumor-infiltrating CD4$^+$ T cells expressing T$_{reg}$ markers (CD25, Foxp3 and Lag-3) in Stat3$^{-/-}$ mice were considerably reduced.

Example 6

Ablation of Stat3 in Hematopoietic Cells Induces Antitumor Effects

Figure 22:
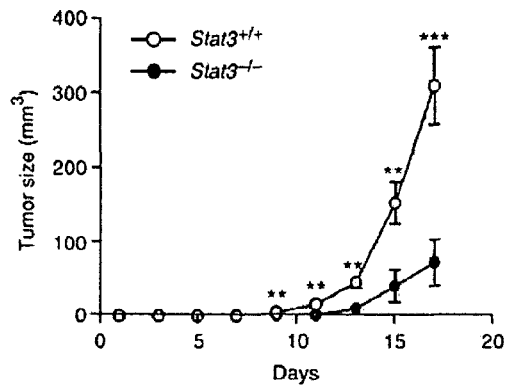
FIG. 22 is a graphical representation of B16 tumor volume over time in Stat3$^{+/+}$ and Stat3$^{-/-}$ mice. Shown are the results representative of three independent experiments; n=10 for each experiment. *P<0.001; P<0.01; *P<0.05.
Figure 23:
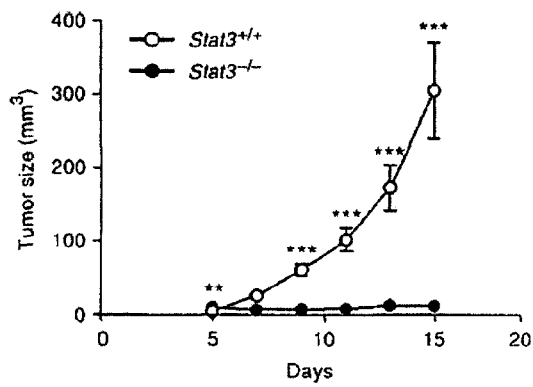
FIG. 23 is a graphical representation of MB49 tumor volume over time in Stat3$^{+/+}$ and Stat3$^{-/-}$ mice. Shown are the results representative for two independent experiments; n=10 for each experiment.

The ability to induce hematopoietic Stat3 ablation in our system permits determination of how Stat3 signaling in hematopoietic cells ultimately affects tumor growth independent of Stat3 activity within tumor cells. As described in Example 1, Stat3 alleles were deleted in hematopoietic cells before subcutaneous tumor challenge 5 days after poly(I:C) administration. FIG. 22 shows that B16 tumor development is significantly inhibited in Stat3$^{-/-}$ mice. FIG. 23 shows that MB49 tumor development is also significantly inhibited.

Figure 24:
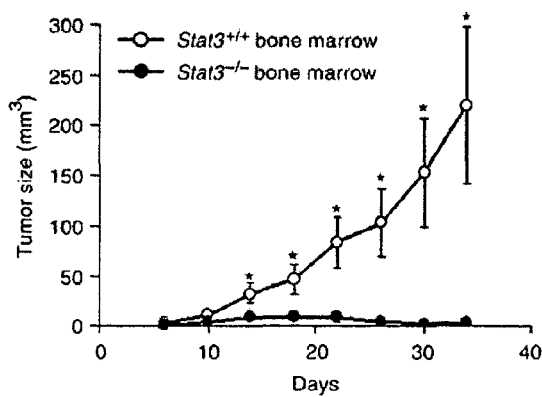
FIG. 24 is a graphical representation of MB49 tumor volume over time in mice engrafted with Stat3$^{+/+}$ and Stat3$^{-/-}$ whole bone marrow.

To prove that the observed antitumor effects were contributed by Stat3 ablation in the hematopoietic compartment, lethally irradiated wild-type recipients were reconstituted with Stat3$^{+/+}$ or Stat3$^{-/-}$ bone marrow. We challenged mice with engrafted Stat3$^{+/+}$ or Stat3$^{-/-}$ bone marrow with MB49 tumors 2 months after bone marrow transplant. As shown in FIG. 24, growth inhibition followed by complete rejection of tumors was observed in mice with reconstituted Stat3$^{-/-}$ bone marrow, whereas tumors in Stat3$^{+/+}$ mice grew progressively. These results confirmed that loss of Stat3 in the hematopoietic system mediates the observed antitumor effects. MB49 tumor growth is abolished in mice engrafted with Stat3$^{-/-}$ whole bone marrow.

Figure 25:
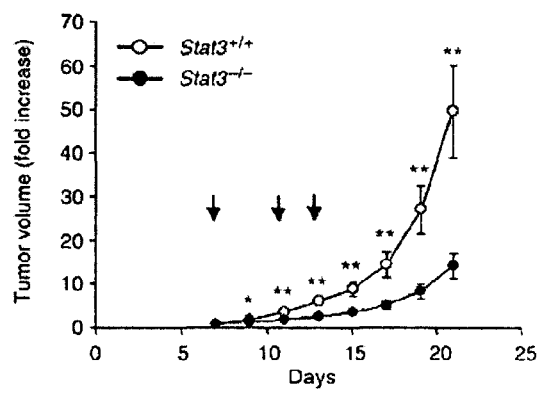
FIG. 25 is a graphical representation of the effects of Stat3 ablation on established B16 tumor growth, n=12.
Figure 26:
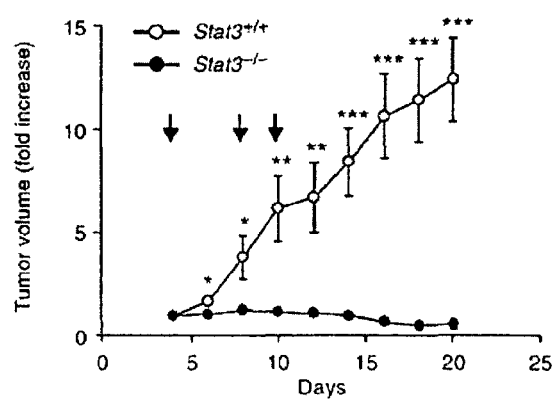
FIG. 26 is a graphical representation of the effects of Stat3 ablation on established MB49 tumors, n=9. Shown are the results of two independent experiments.

To determine whether blocking Stat3 signaling in immune cells would have therapeutic antitumor effects, Stat3$^{loxP/loxP}$ and Cre-Stat3$^{loxP/loxP}$ mice were challenged with B16(F10) tumor cells. When tumors became palpable (average diameter, 4 mm), poly(I:C) was administered to both groups on days 7, 11 and 13. As shown in FIG. 25, ablating the Stat3 alleles in hematopoietic cells led to significant growth inhibition of established B16 tumors. Moreover, as demonstrated in FIG. 26, ablation of Stat3 also induced complete regression of established MB49 tumors. Average tumor diameter was 6 mm on the day of initial poly(I:C) treatment.

Figure 27:
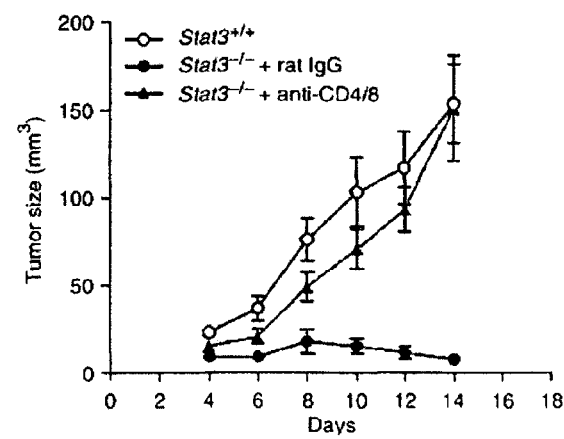
FIG. 27 is a graphical representation of the effects of Stat3 blockade on established tumors in the presence of a control rat IgG or antibodies to CD4 and CD8, as indicated. Statistical significance of the experiment was tested by one-way ANOVA, P=0.0196, n=5. Data are mean numbers±s.e.m.

To determine whether Stat3 blockade-induced antitumor effects require T cells, MB49 tumors were implanted in poly (I:C)-treated Stat3$^{loxP/loxP}$ and Cre-Stat3$^{loxP/loxP}$ mice and Stat3$^{-/-}$ mice were injected with a control rat IgG or antibodies to CD4 and CD8. Results are shown in FIG. 27. Although ablation of the Stat3 alleles in bone marrow cells abrogated MB49 tumor growth as expected, the observed antitumor effects were essentially lost in the absence of CD4$^+$ and CD8$^+$ T cells.

Example 7

Antitumor Effects of Stat3 Ablation is Independent of Autoimmunity

Figure 28:
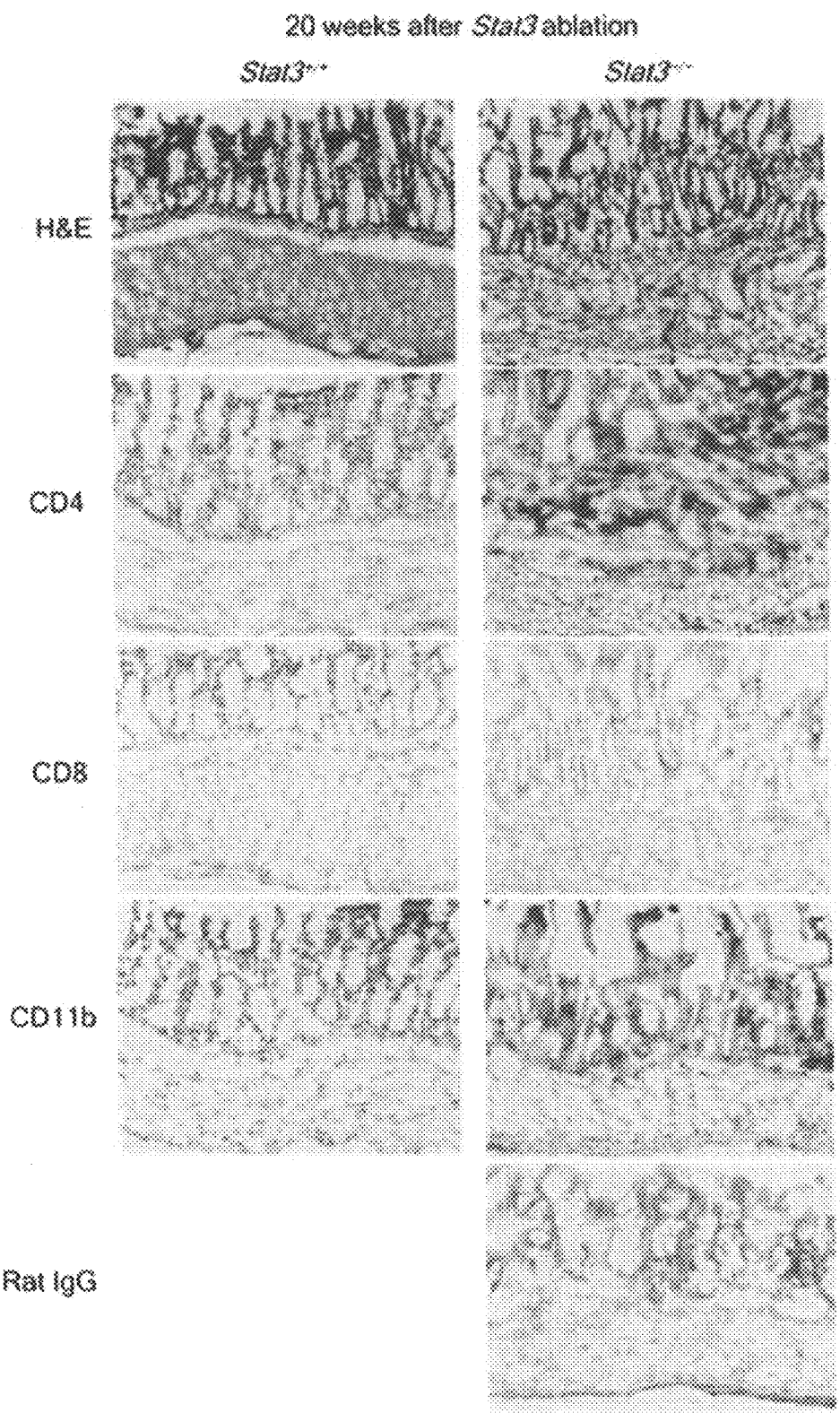
FIG. 28 shows results of immunohistochemical analysis of colon sections from tumor-free Stat3$^{-/-}$ mice 20 weeks after Stat3 ablation (magnification ×40).
Figure 29:
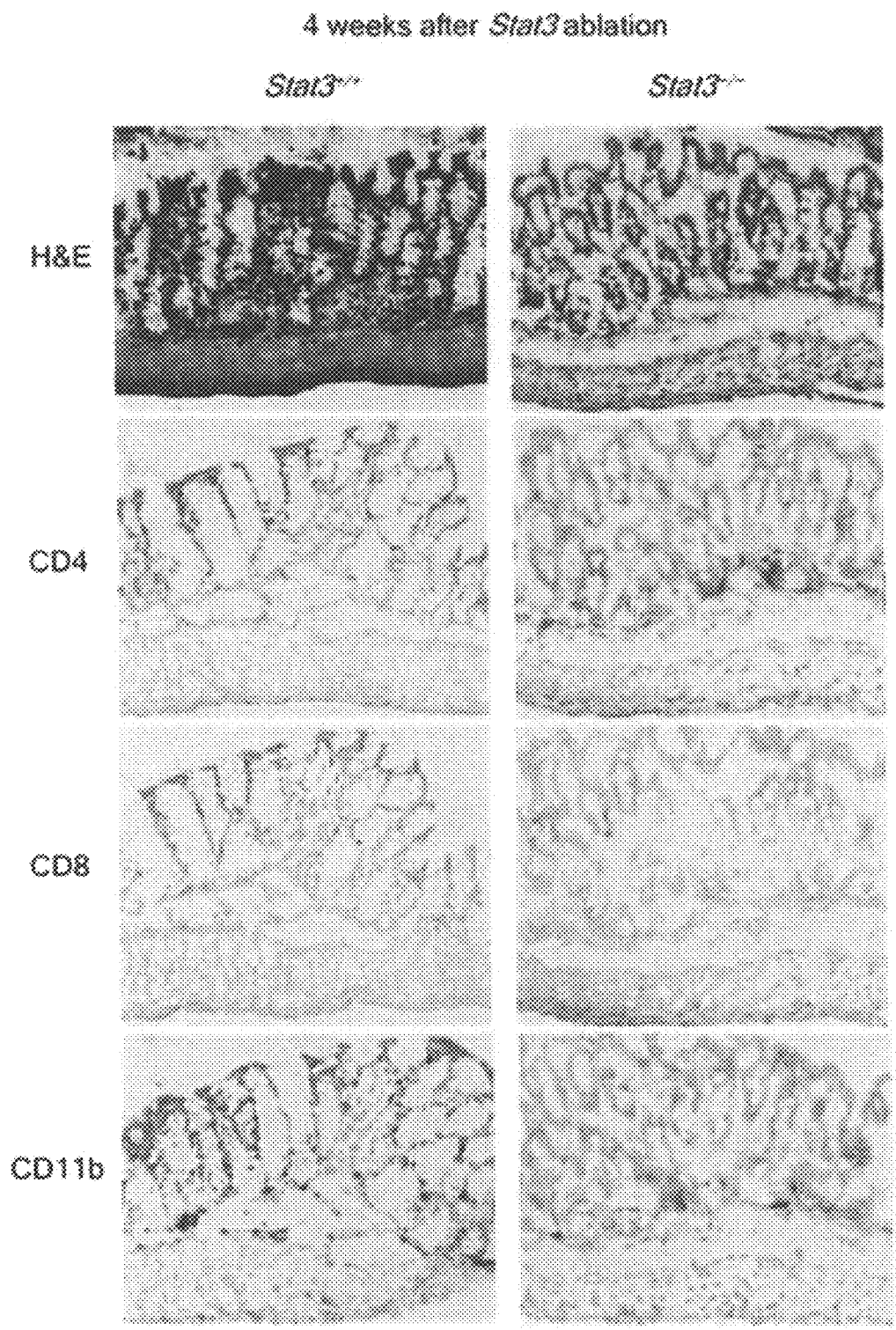
FIG. 29 shows results of immunohistochemical analysis of colon sections from tumor-bearing Stat3$^{+/+}$ and Stat3$^{-/-}$ mice 4 weeks after Stat3 ablation (magnification ×40).
Figure 30:
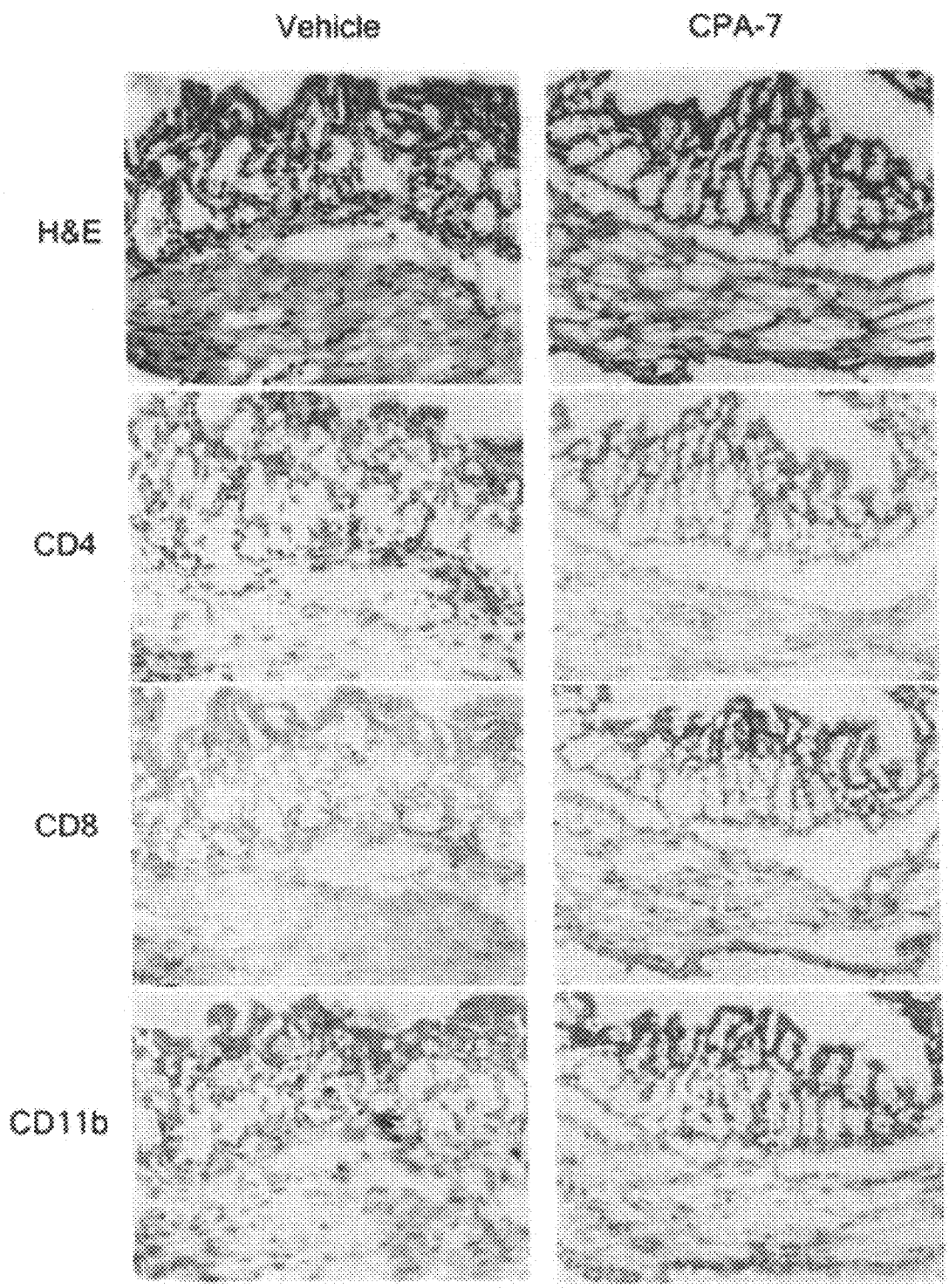
FIG. 30 shows results of immunohistochemical analysis of colon sections from tumor-bearing Stat3$^{+/+}$ and Stat3$^{-/-}$ mice treated with vehicle or CPA-7 (magnification ×40).

Colons from tumor free Stat3$^{-/-}$ mice were evaluated for autoimmune effects at 20 weeks after Stat3 deletion by immunohistochemical analysis. As shown in FIG. 28, Crohn's disease-like pathology was observed, with infiltration by lymphocytes and macrophages. In contrast, there was virtually no evidence of systemic autoimmunity at 4 weeks after induced depletion in tumor-bearing Stat3$^{+/+}$ and Stat3$^{-/-}$ mice (FIG. 29). Similarly, there was a lack of pathologic changes in colons of tumor-bearing Stat3$^{+/+}$ and Stat3$^{-/-}$ mice treated with vehicle or CPA-7 every third day for three weeks (FIG. 30).

This analysis indicates that although Stat3 ablation-induced antitumor immunity is apparent within a week, there was virtually no evidence of systemic autoimmunity, suggesting that the antitumor responses induced by Stat3 ablation are not simply a manifestation of systemic autoimmunity in these mice, but rather a specific effect on intrinsic tumor immune surveillance.

Example 8

Targeting Stat3 with a Small-Molecule Inhibitor Induces Antitumor Immunity

Figure 31:
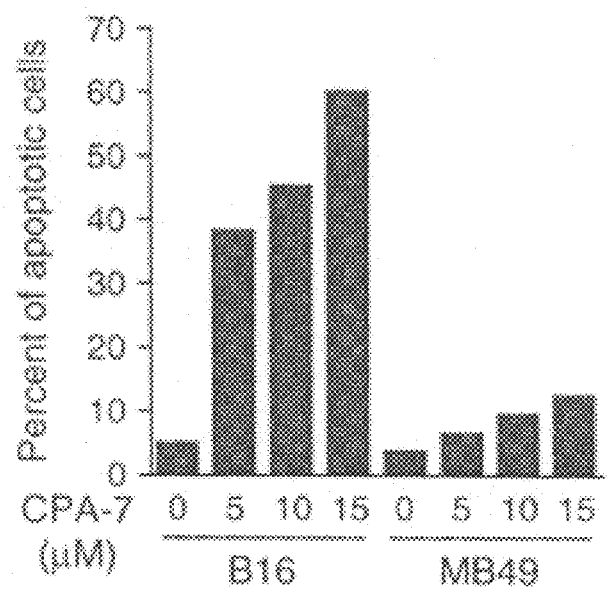
FIG. 31 is a graphical representation showing sensitivity of tumor cells to CPA-7-induced apoptosis in vitro as determined by annexin V staining.

The effects of blocking Stat3 in immune cells with CPA-7, a small-molecule Stat3 inhibitor, were assessed. For these experiments, both B16 and MB49 tumor cells were used. In contrast to B16, MB49 tumor cells are insensitive to CPA-7-induced tumor-cell apoptosis, as determined by annexin V staining. Percentages of apoptotic cells are shown in FIG. 31.

Figure 32:
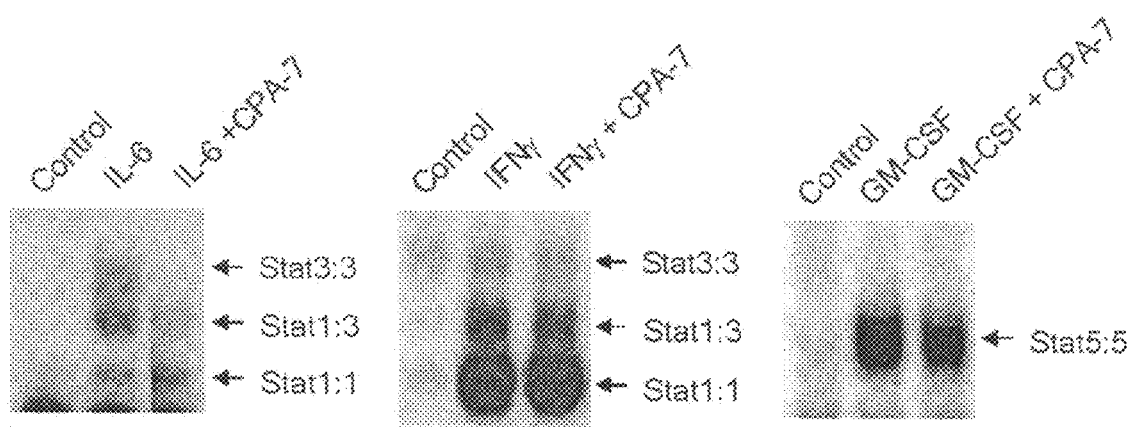
FIG. 32 depicts the results of EMSA analysis of dendritic cells preincubated with CPA-7 overnight and then stimulated with Il-6, IFN-γ or GM-CSF and probed for Stat heterodimers.

Mouse DC2.4 dendritic cells were preincubated with 10 μm CPA-7 overnight and then stimulated for 20 minutes with 20 ng/ml IL-6 (activator of both Stat3 and Stat1), 500 U/ml IFN-γ (activator of Stat5) or 20 ng/ml GM-CSF (activator of Stat5). After cell lysis, nuclear extracts were prepared and EMSA was conducted to detect DNA binding. As shown in FIG. 32, CPA-7 inhibits Stat3 but not Stat1 or Stat5 in dendritic cells.

Figure 33:
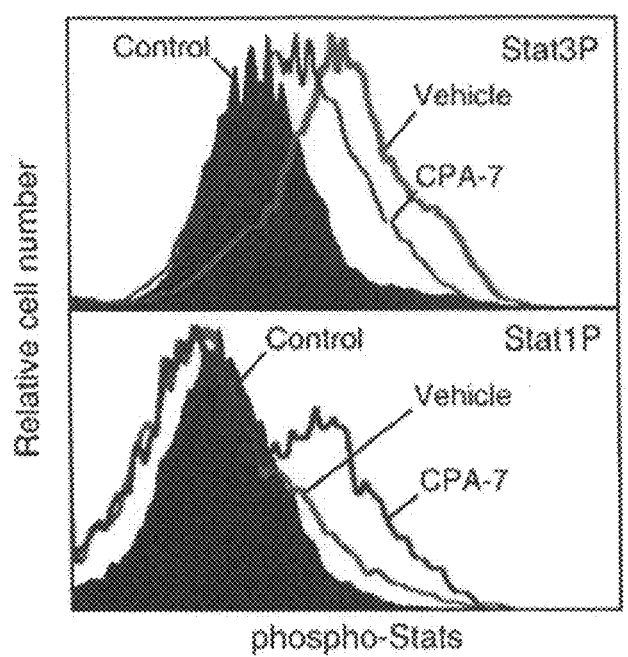
FIG. 33 depicts results of intracellular flow cytometric analysis using an antibody to detect tyrosine-phosphorylated Stat3 (phospho-Stat3). Top panel: Phospho-Stat3 (Stat3P) levels in MB49 tumor-infiltrating DCs. Lower panel: Stat1P levels in tumor-infiltrating DCs.

To further characterize activation of CPA-7 treated immune cells, Phospho-Stat3 (Stat3P) levels in tumor-infiltrating DCs were assessed 24 hours after intravenous injection with vehicle or CPA-7 and compared to splenic $CD11c^+$ cells from tumor-free $Stat3^{+/+}$ mice. As shown in FIG. 33, tumor-infiltrating DCs from the mice receiving CPA-7 showed considerably reduced phosphorylated Stat3 compared to vehicle-treated mice. Also shown in FIG. 33, CPA-7 treated tumor-infiltrating DCs have increased phosphorylated Stat1.

Figure 34:
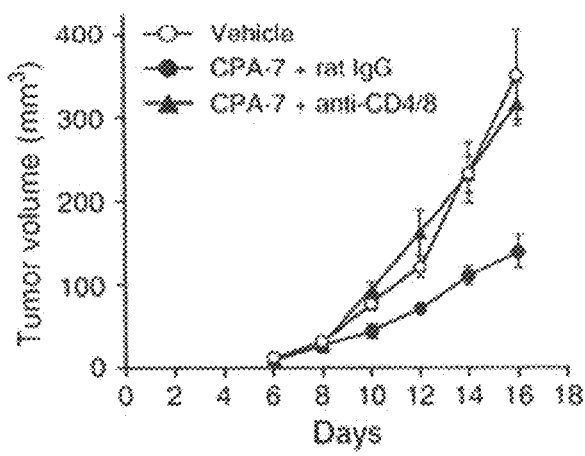
FIG. 34 is a graphical representation of the effects of CPA-7 treatment on established tumors in the presence of a control rat IgG or antibodies to CD4 and CD8, as indicated.; P=0.0088 (by one-way ANOVA), n=6.

Mice with MB49 tumors (about 6 mm in diameter) received intravenous injections of either vehicle or CPA-7. As shown in FIG. 34, blocking Stat3 with CPA-7 inhibits the growth of established tumors. In the absence of $CD4^+$ and $CD8^+$ T cells, CPA-7-induced tumor growth inhibition was abrogated, suggesting a direct role for immune cells in the in vivo antitumor effects of CPA-7.

Figure 35:
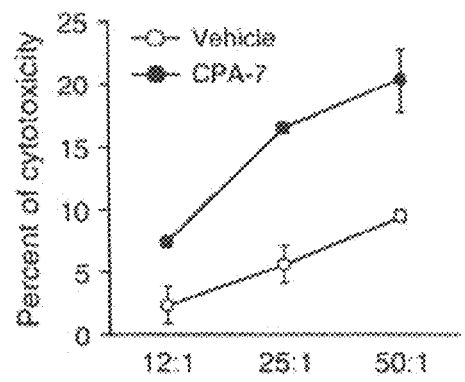
FIG. 35 depicts results of a $^{51}$Cr-release assay to assess activation of NK cell cytotoxicity by CPA-7 using YAC-1 cells as targets; n=3.

Cytotoxicity of CPA-7-treated NK cells from tumor-bearing hosts was assessed using a standard $^{51}Cr$-release assay with YAC-1 cells as targets, as described in Example 1. As shown in FIG. 35, NK cell activity is increased from tumor-bearing mice treated with CPA-7.

Figure 36:
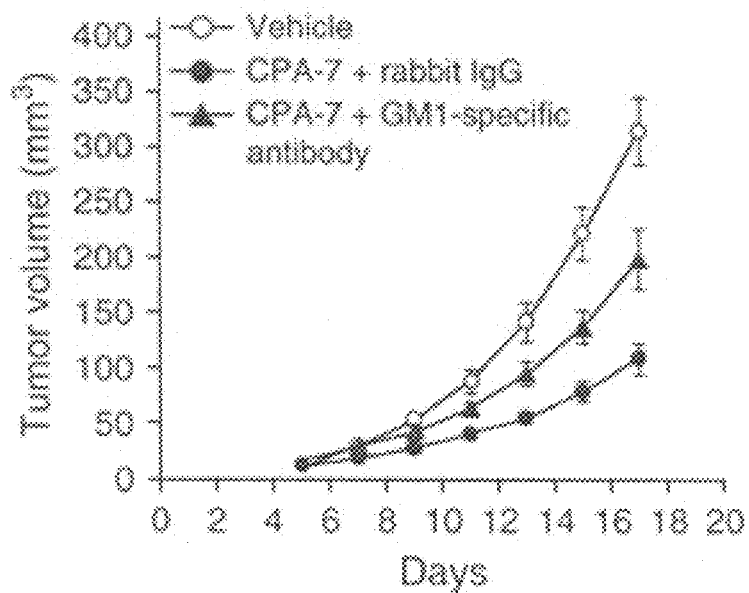
FIG. 36 is a graphical representation of the effects of CPA-7 treatment on established MB49 tumors in the presence of antibody to asialo GM1 or control rabbit IgG, as indicated; P<0.0001 (by one-way ANOVA), n=11.

Mice with established MB49 tumors were treated with vehicle or CPA-7 in combination with control or asialo GM1-specific antibody. As shown in FIG. 36, NK depletion partially abrogates the in vivo antitumor effects of CPA-7 treatment.

Figure 37:
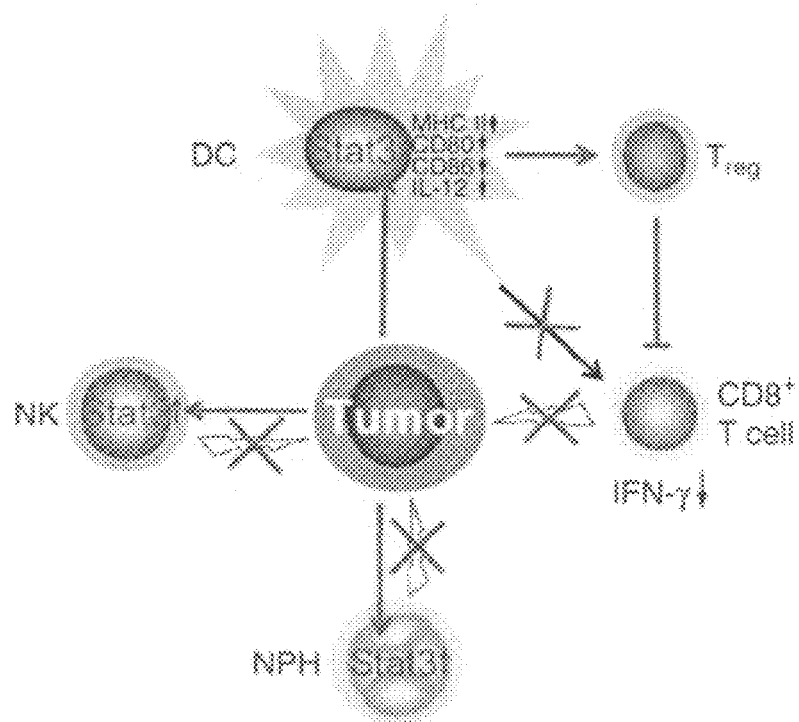
FIG. 37 depicts a schematic overview of Stat3 as a negative regulator of antitumor immunity and potential target for immunotherapy.

Taken together, these data suggest that targeting Stat3 with small-molecule drugs has the potential to induce therapeutic antitumor responses through activating immune cells regardless of the tumors' direct sensitivity to the inhibitors. A schematic overview of Stat3 as a negative regulator of antitumor immunity and potential target for immunotherapy is shown in FIG. 37. As shown, Stat3 activity in tumor-associated NK cells and neutrophils inhibits direct cell cytotoxicity and anti-tumor innate immune responses. Activation of Stat3 in tumor-infiltrating DCs impedes $CD8^+$ T-cell function, and may contribute to accumulation of tolerogenic $T_{reg}$ cells inside tumors.

Example 9

Figure 38:
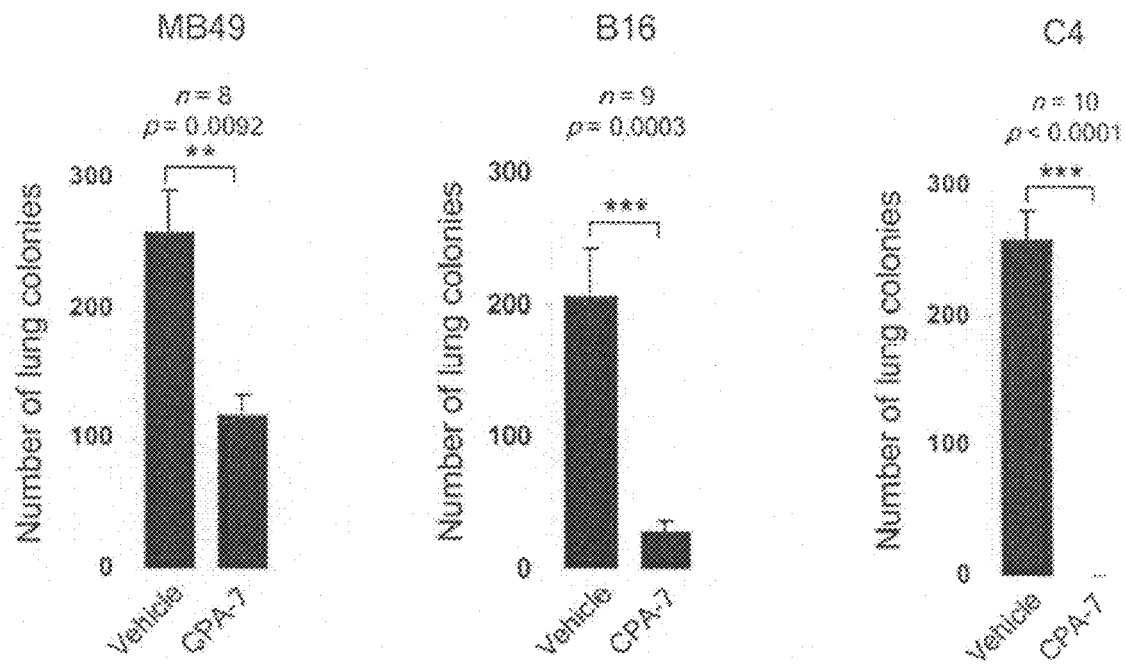
FIG. 38 is a graphical representation of the number of lung nodules in tumor-bearing CPA-7-treated and control mice.
Figure 39:
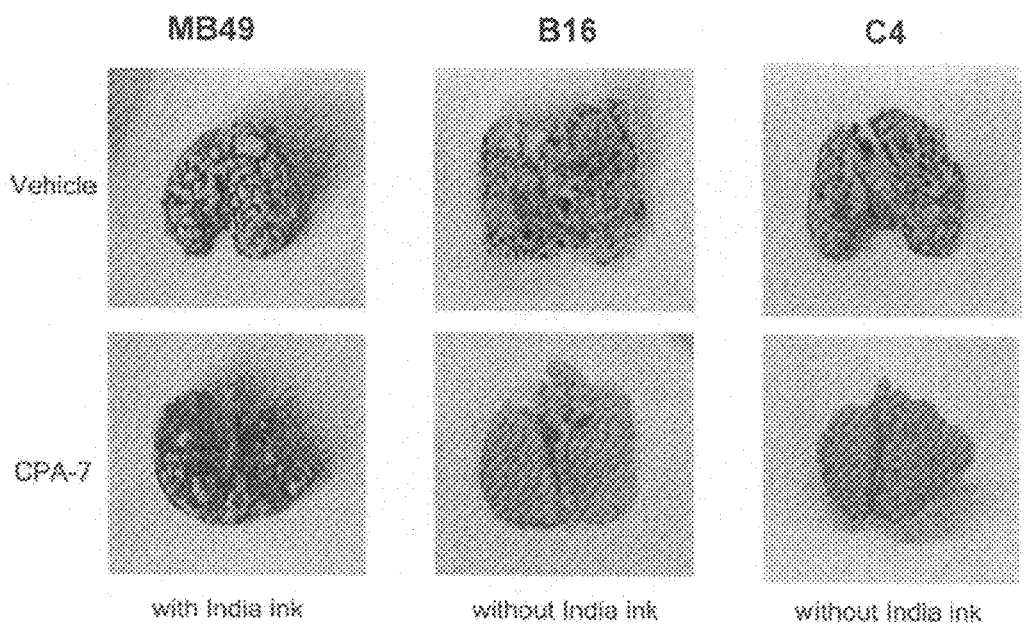
FIG. 39 shows photographs of India ink-stained and unstained lungs from tumor-bearing CPA-7-treated and control mice.

Targeting Stat3 Inhibits Tumor Metastasis and Prolongs Survival of Tumor Bearing Hosts Mice were injected intravenously with $5 \times 10^4$ MB49, B16 or C4 tumor cells, followed by twice weekly treatment with CPA-7 (5 mg/kg) or vehicle (10% DMSO). Lung colonies were enumerated 21 days later, when control mice became moribund. Results, shown in FIG. 38, show that CPA-7 treatment significantly reduced or completely abrogated lung tumor nodules in mice with disseminated tumors.

To visualize lung tumor nodules, lungs were fixed and bleached in Fekete's solution with or without India ink as a counterstain. Representative pictures of excised lungs are shown in FIG. 9.

Figure 40:
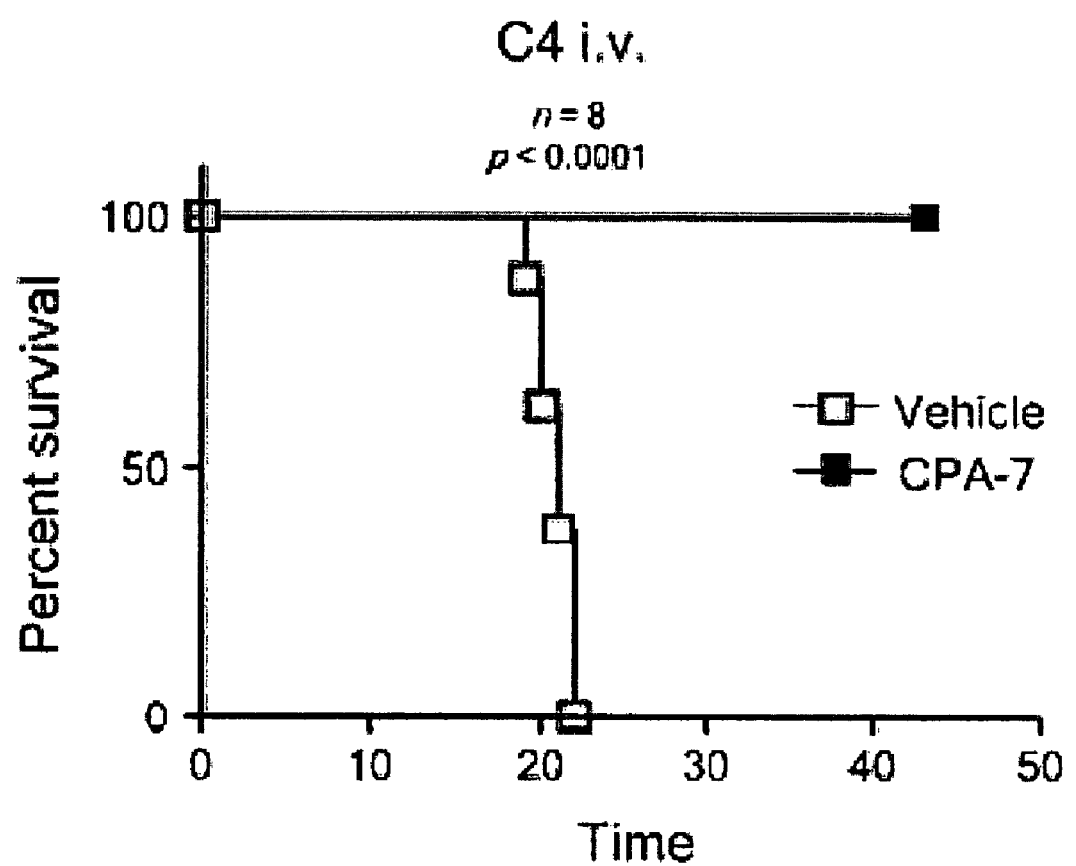
FIG. 40 is a graphical representation showing survival rates of CPA-7 treated and untreated tumor-bearing mice.

Mice injected intravenously with $5 \times 10^4$ C4 tumor cells were treated with CPA-7 twice weekly for three weeks. At three weeks, control mice became moribund and were killed. The CPA-7-treated mice were monitored for the next three weeks. As shown in FIG. 40, CPA-7 treatment significantly improved survival, with 100% of treated mice surviving at the end of six weeks.

Example 10

Combination Therapy Using Targeted Stat3 Inhibitor and Paclitaxel+Cisplatin

A patient diagnosed with ovarian carcinoma is treated with anti-CD8 and anti-Lag3 antibodies conjugated to CPA-7. The antibodies are formulated for intravenous administration and administered in a single bolus injection such that 5 mg/kg CPA-7 is delivered to the patient. The CPA-7/antibody treatment is given every 48 hours for 3 weeks. Commencing 24 hours after the first CPA7/antibody treatment, the patient is also treated with TAXOL (paclitaxel) via intravenous delivery over 24 hours at a dose of 135 mg/m². The paclitaxel treatment is repeated at the end of the CPA-7 dosing schedule.

After the above course of treatment is completed, the patient is evaluated for tumor burden. Treatment is repeated every other month until complete clinical regression of the tumor.

As used in this specification and the appended claims, the singular forms "a," "an," and "the" include plural referents unless the content clearly dictates otherwise. Thus, for example, reference to a composition containing "an inhibitor" includes a mixture of two or more inhibitors. It should also be noted that the term "or" is generally employed in its sense including "and/or" unless the content clearly dictates otherwise.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

The invention has been described with reference to various specific embodiments and techniques. However, it should be understood that many variations and modifications may be made while remaining within the spirit and scope of the invention.

We claim:

1. A method of enhancing antitumor activity of an immune cell, wherein the immune cell is a neutrophil, an NK cell or a tumor-infiltrating lymphocyte, comprising contacting the immune cell with a Stat3 inhibitor, the Stat3 inhibitor conjugated to an antibody specific for a surface marker of the immune cell, wherein the Stat3 inhibitor is a platinum (IV) compound.

2. The method of claim 1, wherein the immune cell is contacted in vitro, ex vivo or in vivo.

3. The method of claim 1, wherein the platinum (IV) compound is CPA-1, CPA-3, CPA-7 or IS3 295.

4. A method of killing a tumor cell or inhibiting tumor growth in a subject comprising contacting an immune cell of the subject with a Stat3 inhibitor, the Stat3 inhibitor conjugated to an antibody specific for a surface marker of the immune cell, wherein the immune cell is a neutrophil, an NK cell or a tumor-infiltrating lymphocyte, wherein the Stat3 inhibitor is a platinum (IV) compound and wherein the Stat3 inhibitor enhances the ability of the immune cell to kill a tumor cell or inhibit tumor growth in a subject.

5. The method of claim 4, wherein the platinum (IV) compound is CPA-1, CPA-3, CPA-7 or IS3 295.

6. The method of claim 4, wherein the immune cell is a tumor-infiltrating lymphocyte.

7. An ex vivo method of killing a tumor cell or inhibiting tumor growth in a subject comprising contacting an isolated tumor-infiltrating lymphocyte with a Stat3 inhibitor, wherein the Stat3 inhibitor is a platinum (IV) compound, and administering the tumor infiltrating lymphocyte to the subject, wherein the Stat3 inhibitor enhances the ability of the tumor infiltrating cell to kill the tumor cell or inhibit tumor growth in the subject.

8. The method of claim 4, further comprising administering a chemotherapeutic agent to the subject.

9. A method of inhibiting tumor growth comprising contacting an immune cell with a Stat3 inhibitor, wherein the Stat3 inhibitor is a platinum (IV) compound the Stat3 inhibitor conjugated to an antibody specific for a surface marker of the immune cell wherein the Stat3 inhibitor enhances the ability of the contacted immune cell to inhibit tumor growth, and wherein the immune cell is a neutrophil, an NK cell or a tumor-infiltrating lymphocyte.

10. The method of claim 9, wherein the contacted immune cell inhibits tumor growth indirectly.

11. The method of claim 1, wherein the immune cell is a neutrophil.

12. The method of claim 1, wherein the immune cell is an NK cell.

13. The method of claim 1, wherein the immune cell is a tumor-infiltrating lymphocyte.

14. The method of claim 4, wherein the immune cell is contacted in vivo.

* * * * *